(12) United States Patent
Chen et al.

(10) Patent No.: US 12,331,007 B2
(45) Date of Patent: Jun. 17, 2025

(54) USE OF A MULTIDENTATE PHOSPHITE LIGAND IN THE CATALYTIC SYNTHESIS OF ADIPONITRILE

(71) Applicants: ZHEJIANG NHU CO., LTD., Zhejiang (CN); ZHEJIANG NHU SPECIAL MATERIALS CO., LTD., Zhejiang (CN); ZHEJIANG NHU NYLON MATERIALS CO., LTD., Zhejiang (CN)

(72) Inventors: Zhirong Chen, Zhejiang (CN); Wenbin Wu, Zhejiang (CN); Hong Yin, Zhejiang (CN); Zengshi Zha, Zhejiang (CN); Keyan Wang, Zhejiang (CN); Li Ma, Zhejiang (CN); Guodong Huang, Zhejiang (CN); Guiyang Zhou, Zhejiang (CN); Yong Xu, Zhejiang (CN)

(73) Assignees: ZHEJIANG NHU CO., LTD., Zhejiang (CN); ZHEJIANG NHU SPECIAL MATERIALS CO., LTD., Zhejiang (CN); ZHEJIANG NHU NYLON MATERIALS CO., LTD., Zhejiang (CN)

( * ) Notice: Subject to any disclaimer, the term of this patent is extended or adjusted under 35 U.S.C. 154(b) by 0 days.

(21) Appl. No.: 17/800,452

(22) PCT Filed: Jun. 21, 2022

(86) PCT No.: PCT/CN2022/100184
§ 371 (c)(1),
(2) Date: Aug. 17, 2022

(87) PCT Pub. No.: WO2023/060929
PCT Pub. Date: Apr. 20, 2023

(65) Prior Publication Data
US 2024/0336560 A1    Oct. 10, 2024

(30) Foreign Application Priority Data

Oct. 15, 2021 (CN) .......................... 202111203682.2

(51) Int. Cl.
| | |
|---|---|
| *C07C 253/10* | (2006.01) |
| *B01J 31/18* | (2006.01) |
| *B01J 37/04* | (2006.01) |
| *C07F 9/06* | (2006.01) |
| *C07F 9/6571* | (2006.01) |

(52) U.S. Cl.
CPC .......... *C07C 253/10* (2013.01); *B01J 31/185* (2013.01); *B01J 37/04* (2013.01); *C07F 9/062* (2013.01); *C07F 9/6571* (2013.01); *B01J 2231/322* (2013.01); *B01J 2231/52* (2013.01); *B01J 2531/004* (2013.01); *B01J 2531/847* (2013.01)

(58) Field of Classification Search
CPC ...... C07C 253/10; C07F 9/062; C07F 9/6571; B01J 31/185
See application file for complete search history.

(56) References Cited

FOREIGN PATENT DOCUMENTS

| | | |
|---|---|---|
| CN | 1159799 A | 9/1997 |
| CN | 1265093 A | 8/2000 |
| CN | 1356335 A | 7/2002 |
| CN | 1387534 A | 12/2002 |
| CN | 101484416 A | 7/2009 |
| CN | 101489992 A | 7/2009 |
| CN | 101676261 A | 3/2010 |
| CN | 102089275 A | 6/2011 |
| CN | 103180290 A | 6/2013 |
| CN | 103664691 A | 3/2014 |
| CN | 103804229 A | 5/2014 |
| CN | 104379590 A | 2/2015 |
| CN | 105188928 A | 12/2015 |
| CN | 111892514 A | 11/2020 |
| CN | 111995547 A | 11/2020 |

(Continued)

*Primary Examiner* — Sikarl A Witherspoon
(74) *Attorney, Agent, or Firm* — Young Basile Hanlon & MacFarlane, P.C.

(57) ABSTRACT

A multidentate phosphite ligand is used in the catalytic synthesis of adiponitrile. The ligand is represented by the following general formula (I). The method of catalytic synthesis of adiponitrile comprises primary hydrocyanation, isomerization, and secondary hydrocyanation reactions, wherein the catalyst adopted each comprises a phosphite ligand-nickel complex composed of a nickel precursor and a multidentate phosphite ligand. The ligand molecule has a higher electron cloud density, and the phosphorus content capable of participating in coordination in the ligand molecule per unit mass is higher, so that the catalytic activity of the catalyst is improved, and the amount of the catalyst is reduced.

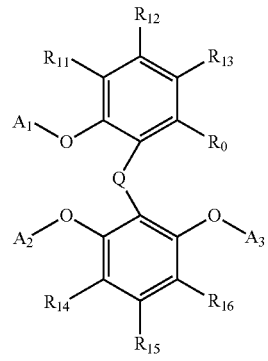

(I)

12 Claims, No Drawings

(56) References Cited

FOREIGN PATENT DOCUMENTS

| | | |
|---|---|---|
| CN | 112794948 A | 5/2021 |
| CN | 113264847 A | 8/2021 |
| CN | 113372239 A | 9/2021 |
| CN | 113416152 A | 9/2021 |
| CN | 113912516 A | 1/2022 |
| WO | 99052632 A1 | 10/1999 |

USE OF A MULTIDENTATE PHOSPHITE LIGAND IN THE CATALYTIC SYNTHESIS OF ADIPONITRILE

CROSS-REFERENCE TO RELATED APPLICATION(S)

This application claims priority to and the benefit of Chinese Patent Application Serial No. 202111203682.2, filed Oct. 15, 2021, the entire disclosure of which is hereby incorporated by reference.

TECHNICAL FIELD

The present disclosure relates to a field of chemical synthesis, and specifically to a use of a multidentate phosphite ligand in the catalytic synthesis of adiponitrile.

BACKGROUND

Adiponitrile (ADN) is a colorless and transparent oily liquid, which is slightly bitter, insoluble in water, and soluble in methanol, ethanol, and chloroform. Adiponitrile is flammable and releases highly toxic gas when it is exposed to high heat, and the molecular formula is $NC(CH_2)_4CN$. Adiponitrile is an important organic chemical intermediate, which is mainly used in the production of hexamethylenediamine which is an intermediate of Nylon 66 by hydrogenation in industry. Adiponitrile is also used in the preparation of caprolactam and other chemical products and is widely used in automotive, engineering plastics, electronics, precision instruments, textile industry, and other fields.

Currently, the methods for preparing adiponitrile in the industry mainly include methods of electrolytic dimerization of acrylonitrile, catalytic ammoniation of adipic acid, and hydrocyanation of butadiene. In addition, in order to recycle the waste of caprolactam, TORAY INDUSTRIES, INC., Japan has developed a method for preparing adiponitrile by hydrolysis of caprolactam, but due to the lack of raw materials, the production capacity is extremely limited.

The method of hydrocyanation of butadiene was developed by Du Pont, USA in the early 1970s, replacing the original chlorination and cyanation process of butadiene. Compared with other methods for preparing adiponitrile, said method has the advantages of raw materials that are readily available, short process route, low cost, low energy consumption, little corrosion to equipment, high product yield, and the like. Currently, this method is recognized to be the most advanced and reasonable process for producing adiponitrile in the world.

Patent applications CN101676261A and CN103180290A each disclose a process for preparing adiponitrile by hydrocyanation of butadiene, comprising the following steps of a first step of reacting butadiene (BD) with HCN under the action of a catalyst to obtain a target product of straight 3-pentenenitrile (3PN) and a by-product of branched 2-methyl-3-butenenitrile (2M3BN); a second step of isomerizing 2M3BN under the action of the catalyst to obtain 3PN; and a third step of subjecting 3PN and HCN to an addition reaction under the action of the catalyst and Lewis acid to obtain a product of adiponitrile (ADN).

Patents CN1387534A, CN1159799A, WO99052632A1, and the like describe that complex catalysts formed by monodentate phosphites, bidentate phosphites, and bidentate phosphoramidite ligands with zero-valent nickel are applicable to the reaction for the production of adiponitrile by butadiene hydrocyanation process. However, the selectivity of the main products (3-pentenenitrile, adiponitrile) of the existing complex catalysts formed by monodentate or bidentate phosphites and nickel still has room for further improvement in catalyzing the hydrocyanation reaction of butadiene to generate 3-pentenenitrile or catalyzing the hydrocyanation reaction of 3-pentenenitrile to generate adiponitrile. In addition, monodentate/bidentate phosphite ligands and complex catalysts thereof should be used in a large amount, are sensitive to air and moisture, are prone to side reactions such as oxidation and hydrolysis, have very high requirements for air and moisture control and equipment in actual industrial production, and greatly increase the actual production cost of adiponitrile.

SUMMARY

Problem to be Solved by the Disclosure

The present disclosure provides a use of a multidentate phosphite ligand in the catalytic synthesis of adiponitrile. The use of said ligand overcomes the problems existing in the prior art. The ligand-nickel catalyst composed of the ligand may catalytically synthesize adiponitrile with higher selectivity, and the amount of the catalyst in the reaction process may be reduced, the loss of the catalyst in the recycling and reusing process may be reduced, the cost of the catalyst is reduced, and the industrialization is facilitated.

Means for Solving the Problems

The present disclosure provides a use of a multidentate phosphite ligand in the catalytic synthesis of adiponitrile and said multidentate phosphite ligand is a compound represented by the following general formula (I), the method of catalytic synthesis of adiponitrile comprises the following steps of:

subjecting butadiene and hydrocyanic acid to a primary hydrocyanation reaction in the presence of a first catalyst; subjecting a branched mononitrile mixture to an isomerization reaction of branched mononitriles in the presence of a second catalyst, wherein the branched mononitrile mixture is separated from a product obtained in the primary hydrocyanation reaction; subjecting a linear mononitrile mixture and hydrocyanic acid to a secondary hydrocyanation reaction in the presence of a third catalyst and a promoter to obtain a product containing adiponitrile, wherein the linear mononitrile mixture is separated from the products obtained in the primary hydrocyanation reaction and the isomerization reaction;

wherein, the first catalyst, the second catalyst, and the third catalyst are identical or different, and each of the catalysts comprises a phosphite ligand-zero-valent nickel complex formed by a nickel precursor and the multidentate phosphite ligand:

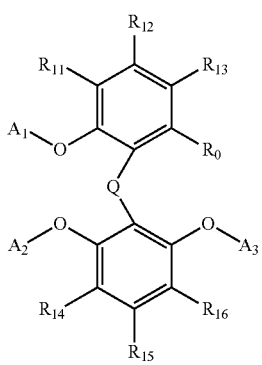

in formula (1), R₀ is —O-A₄, H, an $C_{1\sim6}$ alkyl group, a substituted or unsubstituted $C_{3\sim10}$ cycloalkyl group, or a substituted or unsubstituted $C_{6\sim20}$ aryl group; R₀ is preferably —O-A₄;

R₁₁ to R₁₆ are identical to or different from each other, and each independently represents hydrogen, an $C_{1\sim6}$ alkyl group, a substituted or unsubstituted $C_{3\sim10}$ cycloalkyl group, or a substituted or unsubstituted $C_{6\sim20}$ aryl group; preferably hydrogen, or an $C_{1\sim6}$ alkyl group;

A₁, A₂, A₃, and A₄ are identical to or different from each other, and each independently is

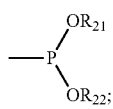

each of R₂₁ and each of R₂₂ are identical to or different from each other, and each of R₂₁ and each of R₂₂ is independently H, a substituted or unsubstituted $C_{1\sim6}$ alkyl group, a substituted or unsubstituted $C_{3\sim10}$ cycloalkyl group, a $C_{1\sim6}$ acyl group, or a substituted or unsubstituted $C_{6\sim20}$ aryl group; preferably H, a substituted or unsubstituted $C_{6\sim20}$ aryl group; more preferably H, a naphthyl group, a methoxy substituted naphthyl group, 1,2,3,4-tetrahydronaphthalene, or

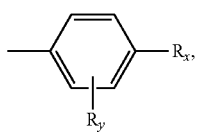

wherein R_x and R_y are identical to or different from each other, and each independently represents hydrogen, halogen, a nitrile group, a substituted or unsubstituted $C_{1\sim10}$ alkyl group, a substituted or unsubstituted $C_{1\sim10}$ alkoxy group; preferably hydrogen, halogen, or an $C_{1\sim6}$ alkyl group; and R₂₁ and R₂₂ may bond to form a ring via a single bond, an $C_{1\sim6}$ alkylene group, a phenylene group, or a $C_{1\sim6}$ alkyl substituted phenylene group;

Q is a single bond, an $C_{1\sim3}$ alkylene group, an oxygen atom, a nitrogen atom, or an $C_{1\sim3}$ alkylene group containing an oxygen atom or a nitrogen atom; preferably a single bond, a methylene group, or an oxygen atom.

According to the use provided by the present disclosure, wherein it is preferable that structures A₁, A₂, A₃, and A₄ in general formula (I) are identical to or different from each other and are each independently one of the following structures:

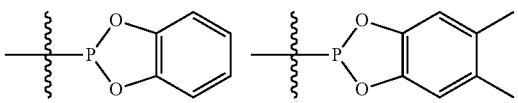

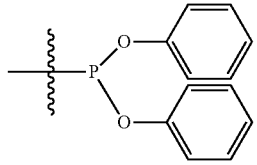

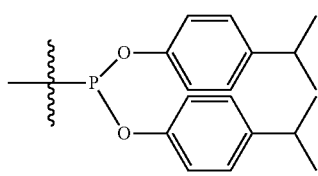

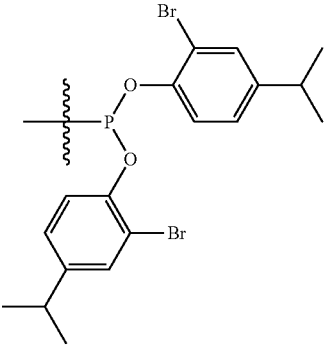

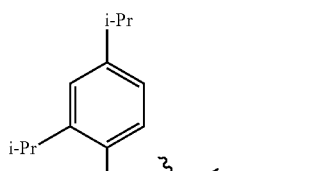

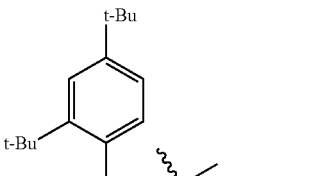

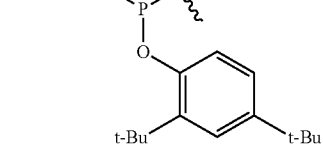

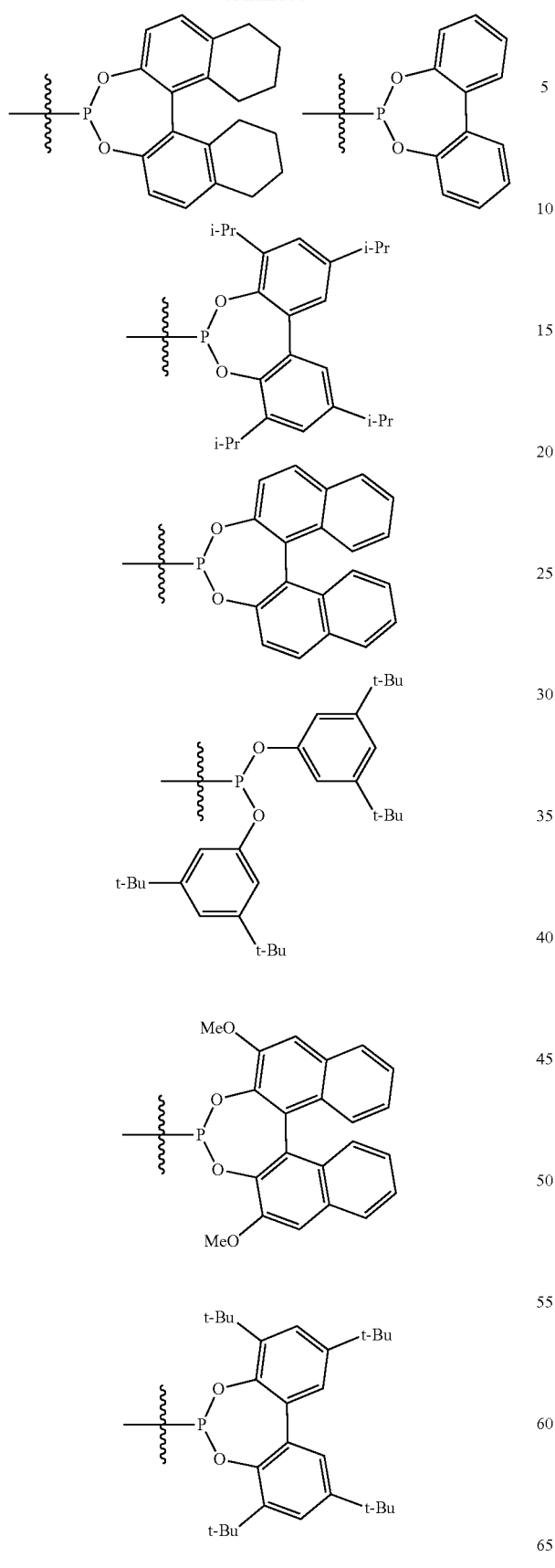
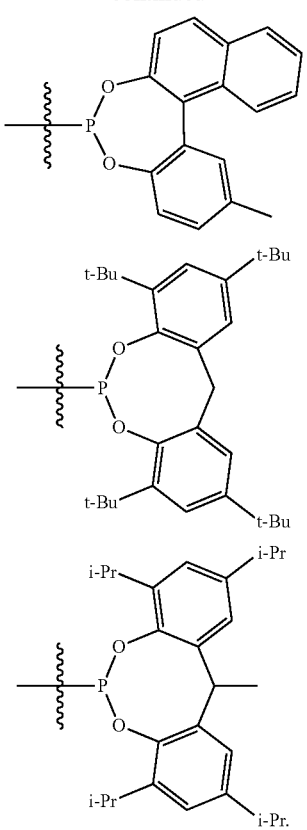
According to the use provided by the present disclosure, wherein it is preferable that the structures $A_1$, $A_2$, $A_3$, and $A_4$ in general formula (I) are each independently one of the following structures:
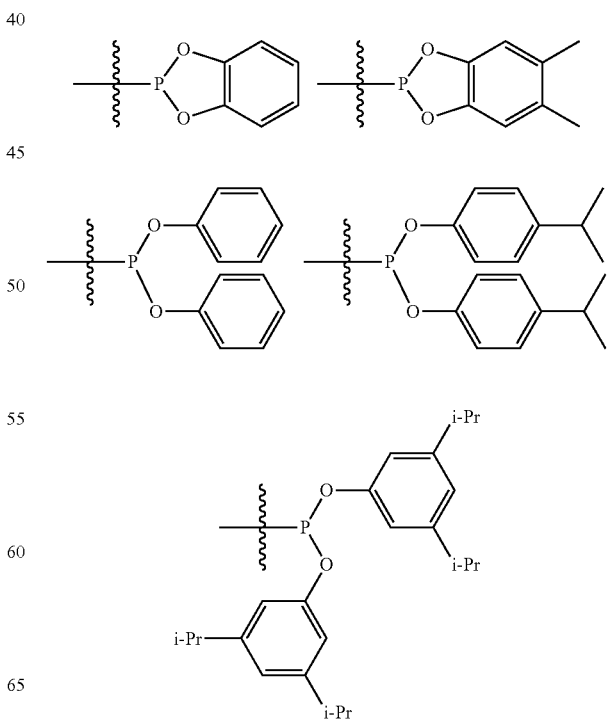

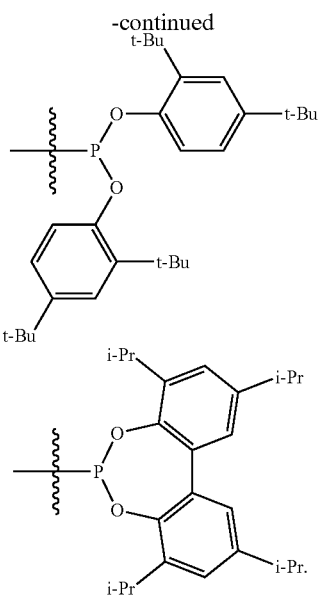

According to the use provided by the present disclosure, wherein it is preferable that at least two of the structures $A_1$, $A_2$, $A_3$, and $A_4$ in general formula (I) are different.

According to the use provided by the present disclosure, wherein it is preferable that in general formula (1), structure $A_1$ is different from structure $A_4$, structure $A_2$ is different from structure $A_3$, structure $A_1$ is identical to structure $A_2$ or $A_3$, and structure $A_4$ is identical to structure $A_3$ or $A_2$.

According to the use provided by the present disclosure, wherein a method for preparing the multidentate phosphite ligand comprises:
reacting a compound represented by the following general formula (II) and at least one halophosphite represented by the general formula (III) with triethylamine in the presence of an organic solvent,

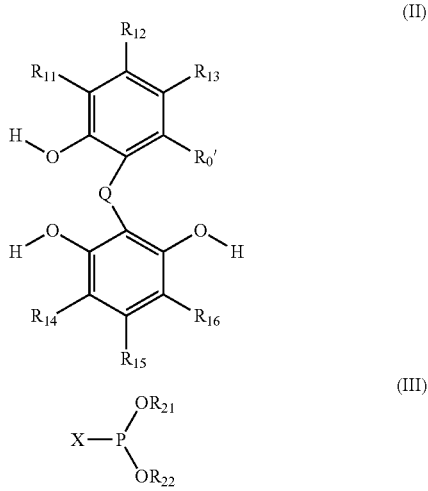

wherein, $R_0'$ represents —OH, H, an $C_{1-6}$ alkyl group, a substituted or unsubstituted $C_{3-10}$ cycloalkyl group, or a substituted or unsubstituted $C_{6-20}$ aryl group; $R_0'$ is preferably —OH; $R_{11}$ to $R_{16}$, $R_{21}$ and $R_{22}$, and Q are as defined in the above general formula (1), and X is halogen, preferably Cl or Br; when the at least one halophosphite represented by general formula (III) is plural, each of $R_{21}$ and each of $R_{22}$ are identical to or different from each other.

According to the use provided by the present disclosure, wherein it is preferable that a ratio of a mole number of the compound represented by general formula (II), the total mole number of at least one halophosphite represented by general formula (III), and the mole number of triethylamine is 1:(3 to 6):(3 to 6).

According to the use provided by the present disclosure, wherein it is preferable that the first catalyst, the second catalyst, and the third catalyst are identical to each other.

According to the use provided by the present disclosure, wherein it is preferable that the molar ratio of the nickel precursor to the multidentate phosphite ligand is 1:(2 to 20).

According to the use provided by the present disclosure, it is preferable that the nickel precursor is one or a mixture of two or more of elemental nickel, bis (1,5-cyclooctadiene) nickel, nickelocene, carbonyl nickel, allyl (cyclopentadienyl) nickel, tetrakis (triphenylphosphine) nickel, bis-triphenylphosphine dicarbonyl nickel, bis (ethylcyclopentadienyl) nickel, di (methylcyclopentadienyl) nickel, bis (tetramethylcyclopentadienyl) nickel, Ni (acac)$_2$, Ni[P (O-o-$C_6H_4CH_3)_3]_3$, and Ni[P (O-o-$C_6H_4CH_3)_3]_2$ ($C_2H_4$), wherein acac is acetylacetone, P (O-o-$C_6H_4CH_3)_3$ is tri (o-tolyl) phosphite; or the nickel precursor is a combination of a divalent nickel compound and a reducing agent, wherein the divalent nickel compound is a halide, a carboxylate, or an acetylacetonate of divalent nickel, and the reducing agent includes a metal borohydride, a metal alanate, a metal alkyl, Li, Na, K, Zn, or $H_2$.

According to the use provided by the present disclosure, wherein it is preferable that in the primary hydrocyanation reaction, the molar ratio of butadiene to hydrocyanic acid is 1.0 to 1.5, the ratio of the mole number of hydrocyanic acid to the mole number of the catalyst in terms of zero-valent nickel is (1 to 1000):1, preferably (10 to 70):1, and a reaction temperature is 60 to 140° C., and a reaction pressure is 0.1 to 5.0 MPa;
in the isomerization reaction of branched mononitriles, the ratio of the mole number of the branched mononitrile mixture to the mole number of the catalyst in terms of zero-valent nickel is (1 to 500):1, preferably (50 to 200):1, and a reaction temperature is 80 to 170° C., and a reaction pressure is 0.1 to 5.0 MPa;
in the secondary hydrocyanation reaction, the molar ratio of the linear mononitrile mixture to the hydrocyanic acid is 1.0 to 1.5, the ratio of the mole number of the hydrocyanic acid to the mole number of the catalyst in terms of zero-valent nickel is (20 to 3000):1, preferably (20 to 500):1, and a reaction temperature is 30 to 120° C., and a reaction pressure is 0.1 to 5.0 MPa.

According to the use provided by the present disclosure, it is preferable that the ratio of the mole number of the promoter to the mole number of the catalyst in terms of zero-valent nickel is (0.05 to 2.5):1, and the promoter is a Lewis acid.

Advantageous Effect of the Disclosure (1) According to the use of the multidentate phosphite ligand in the catalytic synthesis of adiponitrile provided by the present disclosure, wherein the catalyst adopted is a multidentate phosphite ligand-nickel catalyst formed by coordinating a multidentate phosphite ligand with a nickel precursor, wherein the multidentate phosphite ligand has a specific structure. The multidentate phosphite ligand-nickel catalyst exhibits higher reaction selectivity when being used for catalyzing the hydrocyanation reaction to prepare adiponitrile. The highest selectivity for the hydrocyanation reaction of 3-pentenenitrile catalyzed by this catalyst to prepare adiponitrile may be up to 94.2%, and thus the consumption of raw materials and auxiliary materials is reduced.

(2) According to the use of the multidentate phosphite ligand in the catalytic synthesis of adiponitrile provided by the present disclosure, wherein the catalyst adopted is a multidentate phosphite ligand-nickel catalyst formed by coordinating a multidentate phosphite ligand with a nickel precursor, wherein the multidentate phosphite ligand has a specific structure. The multidentate phosphite ligand-nickel catalyst has higher catalytic activity, may reduce the amount of the catalyst used in the reaction process and thus the cost of the catalyst is reduced and the industrialization is facilitated.

(3) According to the use of the multidentate phosphite ligand in the catalytic synthesis of adiponitrile provided by the present disclosure, wherein the catalyst adopted is a multidentate phosphite ligand-nickel catalyst formed by coordinating a multidentate phosphite ligand with a nickel precursor, wherein the multidentate phosphite ligand has a specific structure. The multidentate phosphite ligand-nickel catalyst has better hydrolysis resistance, and thus the loss of the catalyst in the recycling and reusing process may be reduced, the cost of the catalyst is reduced, and the industrialization is facilitated.

DETAILED DESCRIPTION

Hereinafter, specific embodiments of the present disclosure will be described in detail so that the technical solution of the present disclosure will become obvious.

The present disclosure provides a use of a multidentate phosphite ligand in the catalytic synthesis of adiponitrile, and said multidentate phosphite ligand is a compound represented by the following general formula (I), the catalytic synthesis method of adiponitrile comprises the following steps of:

subjecting butadiene and hydrocyanic acid to a primary hydrocyanation reaction in the presence of a first catalyst; subjecting a branched mononitrile mixture to an isomerization reaction of branched mononitriles in the presence of a second catalyst, wherein the branched mononitrile mixture is separated from a product obtained in the primary hydrocyanation reaction; subjecting a linear mononitrile mixture and hydrocyanic acid to a secondary hydrocyanation reaction in the presence of a third catalyst and a promoter to obtain a product containing adiponitrile, wherein the linear mononitrile mixture is separated from the products obtained in the primary hydrocyanation reaction and the isomerization reaction;

wherein the first catalyst, the second catalyst, and the third catalyst are identical or different, and each of the catalysts comprises a phosphite ligand-zero-valent nickel complex formed by a nickel precursor and the multidentate phosphite ligand:

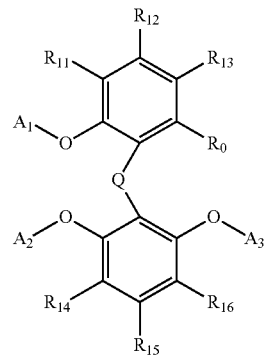

in formula (1), $R_0$ is $-O-A_4$, H, an $C_{1-6}$ alkyl group, a substituted or unsubstituted $C_{3-10}$ cycloalkyl group, or a substituted or unsubstituted $C_{6-20}$ aryl group; $R_0$ is preferably $-O-A_4$;

$R_{11}$ to $R_{16}$ are identical to or different from each other, and each independently represents hydrogen, an $C_{1-6}$ alkyl group, a substituted or unsubstituted $C_{3-10}$ cycloalkyl group, or a substituted or unsubstituted $C_{6-20}$ aryl group; preferably hydrogen, or an $C_{1-6}$ alkyl group;

$A_1$, $A_2$, $A_3$, and $A_4$ are identical to or different from each other, and each independently is

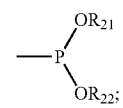

each of $R_{21}$ and each of $R_{22}$ are identical to or different from each other, and each of $R_{21}$ and each of $R_{22}$ is independently H, a substituted or unsubstituted $C_{1-6}$ alkyl group, a substituted or unsubstituted $C_{3-10}$ cycloalkyl group, a $C_{1-6}$ acyl group, or a substituted or unsubstituted $C_{6-20}$ aryl group; preferably H, a substituted or unsubstituted $C_{6-20}$ aryl group; more preferably H, a naphthyl group, a methoxy substituted naphthyl group, 1,2,3,4-tetrahydronaphthalene, or

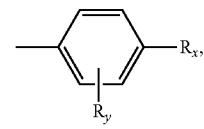

wherein $R_x$ and $R_y$ are identical to or different from each other, and each independently represents hydrogen, halogen, a nitrile group, a substituted or unsubstituted $C_{1-10}$ alkyl group, a substituted or unsubstituted $C_{1-10}$ alkoxy group; preferably hydrogen, halogen, or an $C_{1-6}$ alkyl group; and $R_{21}$ and $R_{22}$ may bond to form a ring via a single bond, an $C_{1-6}$ alkylene group, a phenylene group, or a $C_{1-6}$ alkyl substituted phenylene group;

Q is a single bond, an $C_{1-3}$ alkylene group, an oxygen atom, a nitrogen atom, or an $C_{1-3}$ alkylene group containing an oxygen atom or a nitrogen atom; preferably a single bond, a methylene group, or an oxygen atom.

The multidentate phosphite ligand molecule used in the present disclosure has higher electron cloud density, and the phosphorus content capable of participating in coordination in the multidentate ligand molecule per unit mass is higher, so that the catalytic activity of the multidentate phosphite-nickel complex catalyst containing the ligand is improved, and the amount of the catalyst used in the reaction process is reduced. Meanwhile, the steric and spatial configuration of the phosphite ligand-nickel complex may be adjusted by designing and optimizing the framework structure of the ligand, and the chemical environment and the steric effect around a metal center may be changed by the designing and optimizing mentioned above combined with flexibly regulating the electronic effect and the steric hindrance effect of a substituent on the molecular structure of the ligand, so that the selectivity of a linear product adiponitrile is improved.

The catalyst used in the method of catalytic synthesis of adiponitrile of the present disclosure is a multidentate phosphite ligand-nickel catalyst formed by coordinating a multidentate phosphite ligand with a nickel precursor, wherein the multidentate phosphite ligand has a specific structure. The multidentate phosphite ligand-nickel catalyst has the characteristics of high catalytic activity and high reaction selectivity when being used for preparing the adiponitrile by hydrocyanation reaction, and the highest selectivity for the hydrocyanation reaction of 3-pentenenitrile to prepare the adiponitrile may be up to 94.2%. Moreover, the amount of the catalyst used is less, and the amount of the catalyst used is reduced. In addition, the water resistance of the ligand-nickel complex catalyst is improved compared with the monodentate or bidentate ligand-nickel complex catalyst, the loss of the catalyst or ligand in the recycling and reusing process is reduced, the consumption of the catalyst is reduced, and the cost of the catalyst in the actual industrial production process is reduced.

In a preferred case, structures $A_1$, $A_2$, $A_3$, and $A_4$ in general formula (I) are identical to or different from each other, and is each independently one of the following structures:

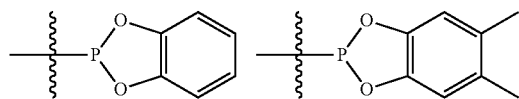

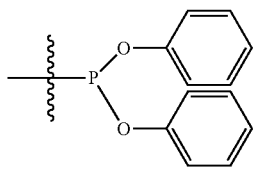

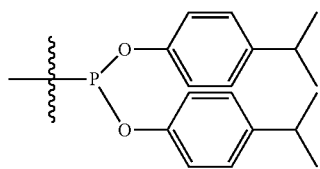

-continued

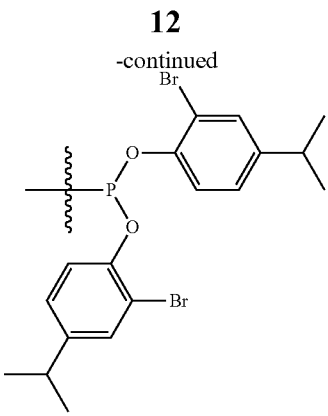

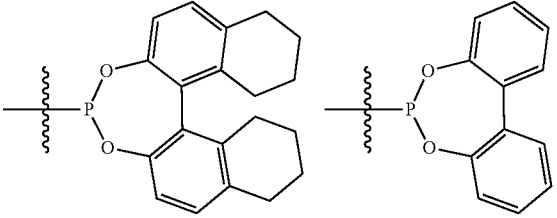

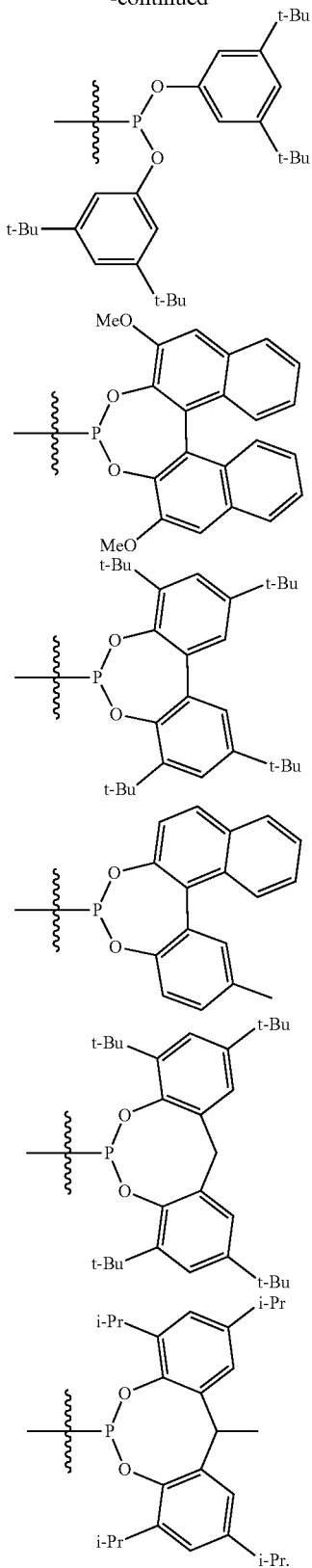

It is more preferred that the structures $A_1$, $A_2$, $A_3$, and $A_4$ in general formula (I) are each independently one of the following structures:

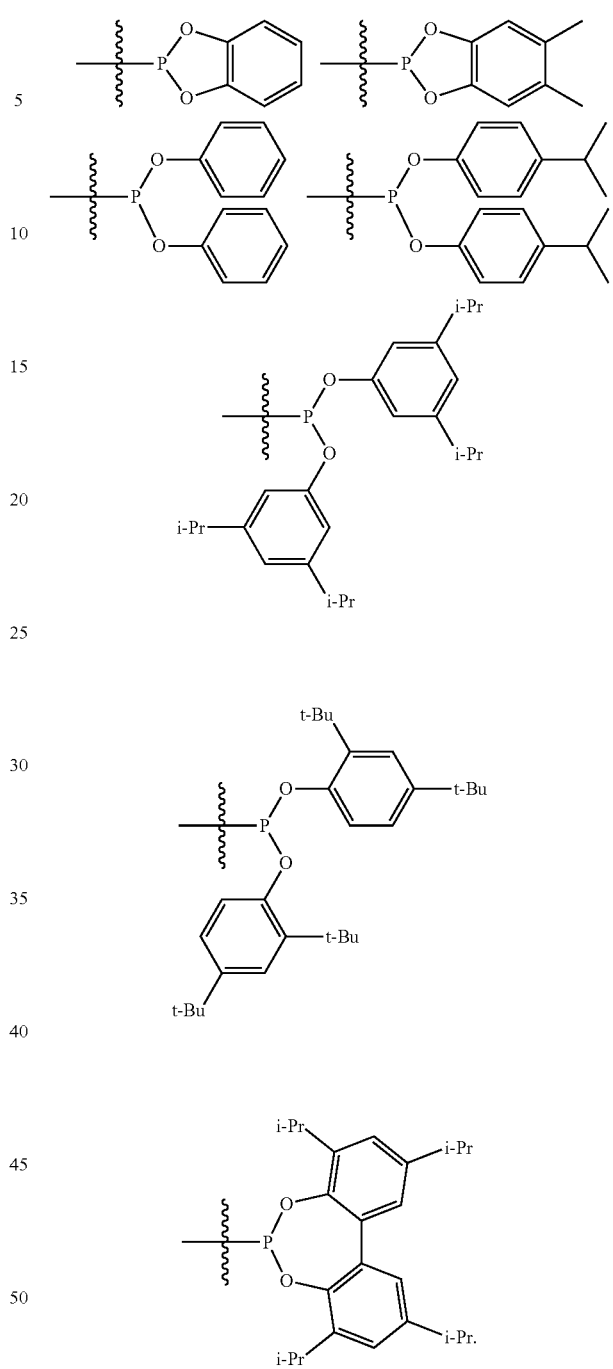

In a preferred case, at least two of the structures $A_1$, $A_2$, $A_3$, and $A_4$ in general formula (I) are different. It is more preferred that structure $A_1$ is different from structure $A_4$, structure $A_2$ is different from structure $A_3$, structure $A_1$ is identical to structure $A_2$ or $A_3$, and structure $A_4$ is identical to structure $A_3$ or $A_2$.

In the method for preparing adiponitrile of the present disclosure, the specific structures of multidentate phosphate ligand in the catalyst used are listed in Table 1 below, however, the multidentate phosphite ligand in the present disclosure is not limited to the following specific multidentate phosphite ligands.

TABLE 1

| Ligand No. | Q | $R_{11}$ | $R_{12}$ | $R_{13}$ | $R_{14}$ | $R_{15}$ | $R_{16}$ | A1 | A2 | A3 | R0 |
|---|---|---|---|---|---|---|---|---|---|---|---|
| L1 | single bond | H | H | H | H | H | H | benzodioxaphosphole | same as A1 | same as A1 | -O-A1 |
| L2 | single bond | H | H | H | H | H | H | P(OPh)$_2$ | same as A1 | same as A1 | -O-A1 |
| L3 | single bond | H | H | H | H | H | H | 3,3',5,5'-tetra-i-Pr-biphenyl dioxaphosphepine | same as A1 | same as A1 | -O-A1 |
| L4 | single bond | H | H | H | H | H | H | P(O-2,4-di-t-Bu-phenyl)$_2$ | same as A1 | same as A1 | -O-A1 |
| L5 | single bond | H | H | H | H | H | H | benzodioxaphosphole | same as A1 | 3,3',5,5'-tetra-i-Pr-biphenyl dioxaphosphepine | -O-A3 |
| L6 | single bond | H | H | H | H | H | H | P(OPh)$_2$ | same as A1 | P(O-2,4-di-t-Bu-phenyl)$_2$ | -O-A3 |

TABLE 1-continued

| Ligand No. | Q | R$_{11}$ | R$_{12}$ | R$_{13}$ | R$_{14}$ | R$_{15}$ | R$_{16}$ | A1 | A2 | A3 | R0 |
|---|---|---|---|---|---|---|---|---|---|---|---|
| L7 | single bond | i-Pr | H | H | H | H | i-Pr | (catecholate phosphite) | same as A1 | bis(2,4-di-i-Pr-phenoxy)phosphite | -O-A3 |
| L8 | single bond | i-Pr | H | H | H | H | i-Pr | (diphenoxy phosphite) | same as A1 | bis(2,4-di-t-Bu-phenoxy)phosphite | -O-A3 |
| L9 | single bond | Me | H | H | H | H | Me | (catecholate phosphite) | same as A1 | biphenyl-bridged bis(i-Pr)phosphite | -O-A3 |
| L10 | single bond | Me | H | H | H | H | Me | (diphenoxy phosphite) | same as A1 | bis(2,4-di-t-Bu-phenoxy)phosphite | -O-A3 |
| L11 | single bond | H | H | H | H | H | H | (4,5-dimethyl-catecholate phosphite) | same as A1 | biphenyl-bridged bis(i-Pr)phosphite | -O-A3 |

TABLE 1-continued

| Ligand No. | Q | $R_{11}$ | $R_{12}$ | $R_{13}$ | $R_{14}$ | $R_{15}$ | $R_{16}$ | A1 | A2 | A3 | R0 |
|---|---|---|---|---|---|---|---|---|---|---|---|
| L12 | single bond | H | H | H | H | H | H | 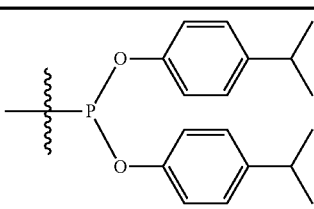 | same as A1 | 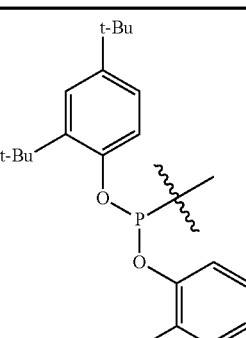 | -O-A3 |
| L13 | single bond | H | H | H | H | H | H | 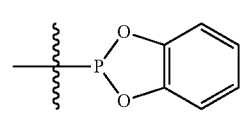 [SMILES: *P1Oc2ccccc2O1] | same as A1 | 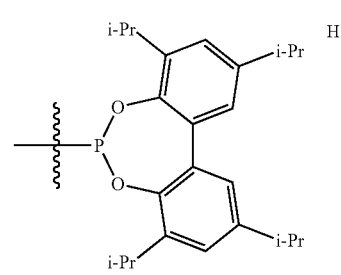 | H |
| L14 | single bond | H | H | H | H | H | H |  | same as A1 |  | H |

The multidentate phosphite ligand contained in the catalyst used in the method for catalytically synthesizing adiponitrile of the present disclosure is preferably a tetradentate phosphite ligand in the general formula (I), wherein structure $A_1$ is different from structure $A_4$, structure $A_2$ is different from structure $A_3$, structure $A_1$ is identical to structure $A_2$ or $A_3$, and structure $A_4$ is identical to structure $A_3$ or $A_2$. The thus obtained catalyst may ensure that the linear selectivity of the obtained adiponitrile product is higher, and the mass amount of the catalyst used in terms of nickel is less.

A method for preparing the multidentate phosphate ligand contained in the catalyst used in the method for catalytically synthesizing adiponitrile of the present disclosure comprises:

reacting a compound represented by the following general formula (II) and at least one halophosphite represented by the general formula (III) with triethylamine in the presence of an organic solvent,

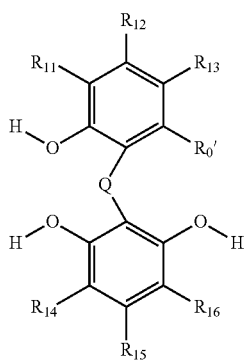

(II)

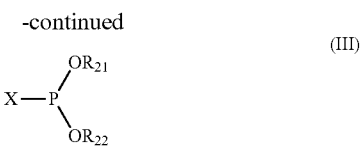

(III)

wherein, $R_0'$ represents —OH, H, an $C_{1\sim6}$ alkyl group, a substituted or unsubstituted $C_{3\sim10}$ cycloalkyl group, or a substituted or unsubstituted $C_{6\sim20}$ aryl group; $R_0'$ is preferably —OH; $R_{11}$ to $R_{16}$, $R_{21}$ and $R_{22}$, and Q are as defined in the above general formula (1), and X is halogen, preferably Cl or Br; when the at least one halophosphite represented by general formula (III) is plural, each of plural $R_{21}$ and each of $R_{22}$ are identical to or different from each other.

The specific method for preparing the multidentate phosphite ligand comprises the following steps of: acquiring the compound represented by above formula (II), at least one halophosphite represented by formula (III) and triethylamine based on the molar ratio of 1:(3 to 6):(3 to 6), dissolving the compound of formula (II) in an organic solvent (such as toluene, tetrahydrofuran and the like), dropwise adding a solution of at least one halophosphite represented by formula (III) and triethylamine in the organic solvent (such as toluene, tetrahydrofuran and the like) at a temperature of −10° C. to 10° C. (or dissolving at least one halophosphite represented by formula (III) in the organic solvent (such as toluene, tetrahydrofuran and the like), and dropwise adding a solution of the compound represented by the formula (II) and triethylamine in the organic solvent (such as toluene, tetrahydrofuran and the like) at a temperature of −10° C. to 10° C.), and continuously stirring the reaction solution at 10 to 50° C. for 2 to 10 hours. After the reaction is completed, triethylamine hydrochloride is removed by filtration, the solvent is removed, and the multidentate phosphite ligand is separated and obtained by column chromatography.

In the method for catalytically synthesizing adiponitrile of the present disclosure, in a preferred case, the first catalyst, the second catalyst, and the third catalyst are identical to each other.

In the method for catalytically synthesizing adiponitrile of the present disclosure, the method for preparation of the catalyst may include contacting a multidentate phosphite ligand with nickel precursor which is elemental nickel or a zero-valent nickel complex having an easily substituted ligand to form the catalyst. The specific preparation method comprises the following steps:

respectively acquiring the nickel precursor and the multidentate phosphite ligand based on the molar ratio of 1:(0.5 to 10), dissolving them in an organic solvent (such as toluene, propionitrile, 3-pentenenitrile, and the like), keeping the temperature at 50° C., stirring and reacting for 5 to 15 hours. After the reaction is completed, the corresponding catalyst is obtained by directly removing the solvent or cooling and recrystallizing.

The above nickel precursor is elemental nickel or zero-valent nickel complex. Examples of these zero-valent nickel complexes include one or a mixture of two or more of bis (1,5-cyclooctadiene) nickel, nickelocene, carbonyl nickel, allyl (cyclopentadienyl) nickel, tetrakis (triphenylphosphine) nickel, bis-triphenylphosphine dicarbonyl nickel, bis (ethylcyclopentadienyl) nickel, di (methylcyclopentadienyl) nickel, bis (tetramethylcyclopentadienyl) nickel, Ni (acac)$_2$, Ni[P (O-o-C$_6$H$_4$CH$_3$)$_3$]$_3$, Ni[P (O-o-C$_6$H$_4$CH$_3$)$_3$]$_2$ (C$_2$H$_4$), and the like (wherein, acac is acetylacetone, P (O-o-C$_6$H$_4$CH$_3$)$_3$ is tri (o-tolyl) phosphite); optionally, a combination of a divalent nickel compound and a reducing agent may be used in place of or in combination with the nickel precursor described above to serve as a source of zero-valent nickel in the reaction in the presence of the multidentate phosphate ligand of formula (I). Suitable divalent nickel compounds include a halide, a carboxylate, or an acetylacetonate of divalent nickel; suitable reducing agents include a metal borohydride, a metal alanate, a metal alkylide, Li, Na, K, Zn, or H$_2$.

In the method for preparing adiponitrile of the present disclosure, in the primary hydrocyanation reaction, the molar ratio of butadiene to hydrocyanic acid is 1.0 to 1.5, the ratio of the mole number of hydrocyanic acid to the mole number of the catalyst in terms of zero-valent nickel is (1 to 1000):1, preferably (10 to 70):1, and a reaction temperature is 60 to 140° C., a reaction pressure is 0.1 to 5.0 MPa, and a reaction time is 0.1 to 5.0 hours;

in the isomerization reaction of branched mononitriles, the ratio of the mole number of the branched mononitrile mixture to the mole number of the catalyst in terms of zero-valent nickel is (1 to 500):1, preferably (50 to 200):1, and a reaction temperature is 80 to 170° C., a reaction pressure is 0.1 to 5.0 MPa, and a reaction time is 0.1 to 10.0 hours;

in the secondary hydrocyanation reaction, the molar ratio of the linear mononitrile mixture to the hydrocyanic acid is 1.0 to 1.5, the ratio of the mole number of the hydrocyanic acid to the mole number of the catalyst in terms of zero-valent nickel is (20 to 3000):1, preferably (20 to 500):1, and a reaction temperature is 30 to 120° C., a reaction pressure is 0.1 to 5.0 MPa, and a reaction time is 1.0 to 20.0 hours.

In the method for preparing adiponitrile of the present disclosure, the ratio of the mole number of the reaction promoter to the mole number of the catalyst in terms of zero-valent nickel is (0.05 to 2.5):1, and the promoter is a Lewis acid.

Lewis acid as a reaction promoter is selected from the group consisting of salts of element selected from Groups Ib, IIb, IIIa, IIIb, IVa, IVb, Va, Vb, VIb, VIIb, and VIII of the Periodic Table of the Elements, and the salt is selected from a halide, a sulfate, a sulfonate, a haloalkylsulfonate, a perhaloalkylsulfonate, a haloalkylacetate, a perhaloalkylacetate, a carboxylate, and a phosphate;

Preferably, the Lewis acid is selected from zinc chloride, zinc bromide, zinc iodide, manganese chloride, manganese bromide, cadmium chloride, cadmium bromide, stannous chloride, stannous bromide, stannous sulfate, stannous tartrate, indium trifluoromethanesulfonate, indium trifluoroacetate, zinc trifluoroacetate, chlorides or bromides of rare earth elements such as lanthanum, cerium, praseodymium, neodymium, samarium, europium, gadolinium, terbium, dysprosium, hafnium, erbium, thallium, ytterbium and lutetium, cobalt chloride, ferric chloride, and yttrium chloride, and mixtures thereof;

More preferably, the Lewis acid is at least one of zinc chloride, zinc bromide, ferric chloride, stannous chloride, and stannous bromide.

The present disclosure is described below by means of examples, but the present disclosure is by no means limited to the following examples.

Example 1

Preparation of Tetradentate Phosphite Ligand L1:

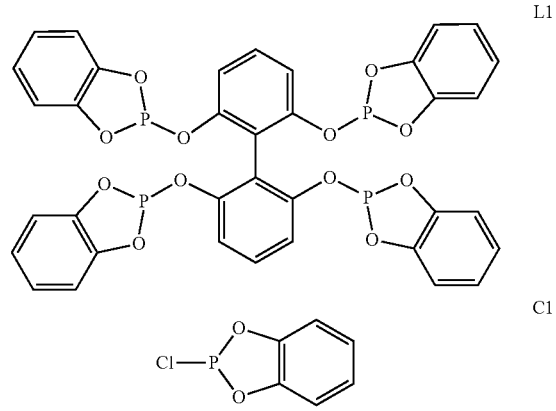

A toluene (150 mL) solution containing 2,2',6,6'-tetrahydroxybiphenyl (4.36 g, 20 mmol) and triethylamine (11.33 g, 112 mmol) was added dropwise to a toluene solution containing chlorophosphite C1 (18.96 g, 100 mmol) represented by formula C1 at 5° C. After the addition was completed, the temperature of the reaction system was kept at 5° C., and the reaction was continued for 2 hours under stirring, and the system was slowly raised to 25° C. and continuously stirred for 2 hours. Subsequently, the reaction solution was filtered to remove triethylamine hydrochloride, toluene was then removed, and then ligand L1 (13.72 g) was obtained after separation and purification by column chromatography (eluent: ethyl acetate/n-hexane=1/200 to 1/100), the yield was 86.1%, and the purity (in mass percent) was 96.7%.

Preparation of Tetradentate Phosphite Ligand-Nickel Catalyst A 10.3 mmol of tetradentate phosphite ligand L1 and 20 mmol of bis (1,5-cyclooctadiene) nickel were added to 100 mL of toluene under nitrogen atmosphere. Next, the reaction system was mixed and allowed to react at 50° C. for 10 hours. After the reaction was completed, the solvent was removed to directly obtain catalyst A, and the nickel content thereof was 1.82 mmol/g.

Preparation of Adiponitrile (i) Primary Hydrocyanation Reaction of Butadiene 2.5 mol of butadiene (BD) was added into a reactor charged with 5.0 mmol (in terms of the mole number of nickel) of tetradentate phosphite ligand-nickel catalyst A, and 2.0 mol of HCN was slowly added under the conditions of the reaction temperature of 60 to 90° C. and the reaction pressure of 2.0 MPa. After the addition was completed, the reaction was continued for 1.0 hour. After the reaction was completed, a sample was taken for analyzing the distribution of products by GC.

As a result of the analysis, >99.9% of starting HCN was converted to 3-pentenenitrile (3PN) and 2-methyl-3-butenenitrile (2M3BN), and the total selectivity of 3PN and 2M3BN was 96.5%. Meanwhile, the ratio of 3-pentenenitrile (3PN) to 2-methyl-3-butenenitrile (2M3BN) was 72.3/27.7 (3PN/2M3BN).

(ii) Isomerization of 2-Methyl-3-Butenenitrile (2M3BN):

2M3BN was obtained from the reaction product of step (1), and 1.5 mol of 2M3BN was added into a reactor charged with 3.0 mmol (in terms of the mole number of nickel) of tetradentate phosphite ligand-nickel catalyst A, and the mixture was reacted under the conditions of the reaction temperature of 120 to 150° C. and the reaction pressure of 1.2 MPa for 8 to 10 hours. After the reaction was completed, a sample was taken for analyzing the distribution of products 3PN and 2M3BN by GC (with valeronitrile as the internal standard).

As a result, the conversion of 2M3BN was 93.2% and the selectivity for 3PN was 95.0%.

(iii) Secondary Hydrocyanation Reaction of 3-Pentenenitrile (3PN):

The 3PN product separated in step (i) and step (ii) was collected, 2.5 mol of 3PN and 10.0 mmol of anhydrous zinc chloride as a reaction promoter were added to a reactor charged with 7.5 mmol (in terms of the mole number of nickel) of tetradentate phosphite ligand-nickel catalyst A, and 2.0 mol of HCN was slowly dropped under the conditions of the reaction temperature of 60 to 80° C. and the reaction pressure of 1.2 MPa. After the reaction was completed, a sample was taken for analyzing the distribution of products by GC.

The following results were analyzed for a percent yield of converting to adiponitrile (ADN) product based on HCN and selectivity to linear adiponitrile expressed as a percent of ADN in the reaction mixture.

As a result, >99.9% of HCN was converted to adiponitrile and its analogues, and the selectivity for linear ADN was 83.1%.

Examples 2 to 4

Preparation of Tetradentate Phosphite Ligands L2 to L4:

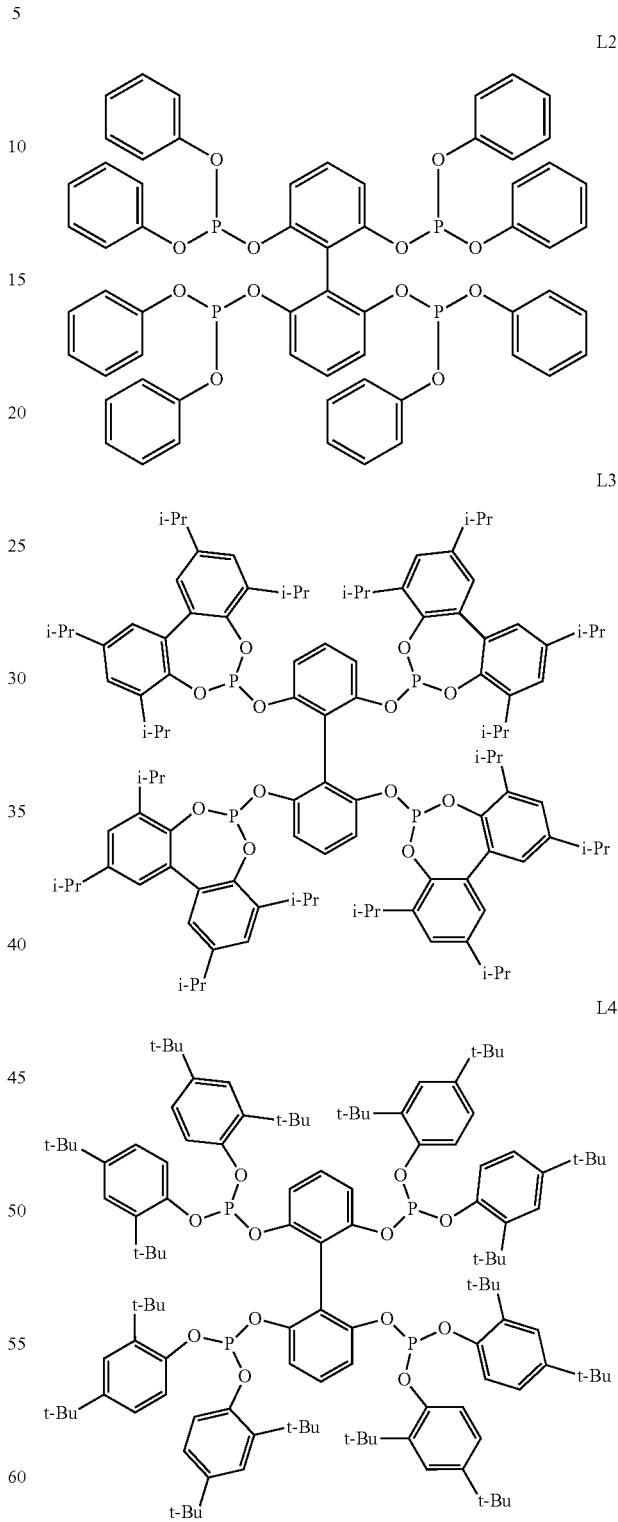

Tetradentate phosphite ligands L2 to L4 were prepared in accordance with the preparation method of tetradentate phosphite ligand L1 in Example 1, except that the toluene solution containing chlorophosphite C1 was changed to toluene solutions containing chlorophosphites C2 to C4 represented by the formulae C2 to C4, respectively, and the amounts of product obtained, yields, and purities are shown in Table 2.

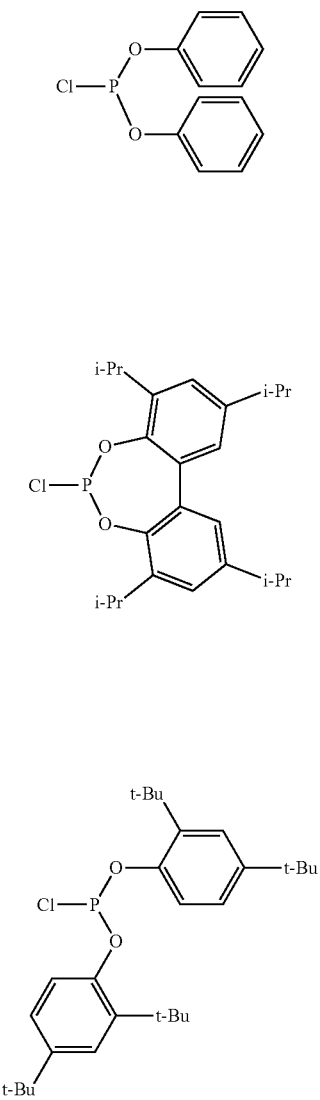

Preparation of Tetradentate Phosphite Ligand-Nickel Catalysts B to D

Tetradentate phosphite ligand-nickel catalysts B to D were prepared in accordance with the preparation method of tetradentate phosphite ligand-nickel catalyst A in Example 1, except that the tetradentate phosphite ligand L1 was changed to the tetradentate phosphite ligands L2 to L4 obtained above, respectively, and the Ni content of the obtained catalyst is shown in Table 2.

Preparation of Adiponitrile

Preparation and analysis were carried out in the same manner as in Example 1 except that catalysts B to D were used, respectively.

Example 5

Preparation of Tetradentate Phosphite Ligand L5:

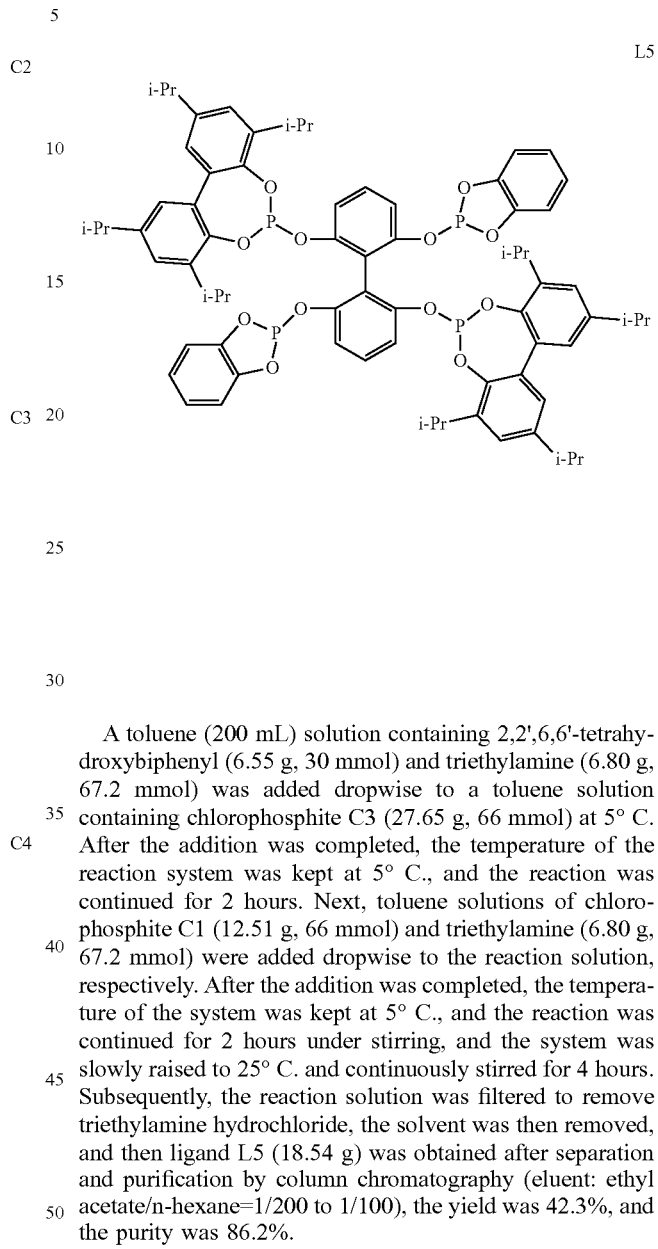

A toluene (200 mL) solution containing 2,2',6,6'-tetrahydroxybiphenyl (6.55 g, 30 mmol) and triethylamine (6.80 g, 67.2 mmol) was added dropwise to a toluene solution containing chlorophosphite C3 (27.65 g, 66 mmol) at 5° C. After the addition was completed, the temperature of the reaction system was kept at 5° C., and the reaction was continued for 2 hours. Next, toluene solutions of chlorophosphite C1 (12.51 g, 66 mmol) and triethylamine (6.80 g, 67.2 mmol) were added dropwise to the reaction solution, respectively. After the addition was completed, the temperature of the system was kept at 5° C., and the reaction was continued for 2 hours under stirring, and the system was slowly raised to 25° C. and continuously stirred for 4 hours. Subsequently, the reaction solution was filtered to remove triethylamine hydrochloride, the solvent was then removed, and then ligand L5 (18.54 g) was obtained after separation and purification by column chromatography (eluent: ethyl acetate/n-hexane=1/200 to 1/100), the yield was 42.3%, and the purity was 86.2%.

Preparation of Tetradentate Phosphite Ligand-Nickel Catalyst E 11.6 mmol of tetradentate phosphite ligand L5 and 20 mmol of bis (1,5-cyclooctadiene) nickel were added to 100 mL of toluene under a nitrogen atmosphere. Next, the reaction system was mixed and allowed to react at 50° C. for 10 hours. After the reaction was completed, the solvent was removed, and tetradentate phosphite ligand-nickel complex catalyst E was obtained by recrystallizataion from acetonitrile solvent upon cooling, and the nickel content of catalyst E was 1.33 mmol/g.

Preparation of Adiponitrile

Preparation and analysis were carried out in the same manner as in Example 1 only except that catalyst E was used.

27

Example 6

Preparation of Tetradentate Phosphite Ligand L6:

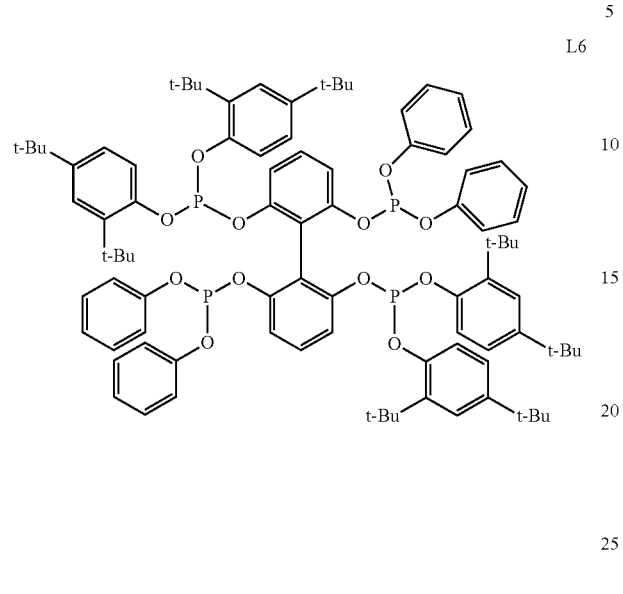

A toluene solution (200 mL) containing 2,2',6,6'-tetrahydroxybiphenyl (6.55 g, 30 mmol) and triethylamine (6.80 g, 67.2 mmol) was added dropwise to a toluene solution containing chlorophosphite $C_4$ (31.49 g, 66 mmol) at 5° C. After the addition was completed, the temperature of the reaction system was kept at 5° C., and the reaction was continued for 2 hours. Next, toluene solutions of chlorophosphite $C_2$ (16.67 g, 66 mmol) and triethylamine (6.80 g, 67.2 mmol) were added dropwise to the reaction solution, respectively. After the addition was completed, the temperature of the system was kept at 5° C., and the reaction was continued for 2 hours under stirring, and the system was slowly raised to 25° C. and continuously stirred for 4 hours. Subsequently, the reaction solution was filtered to remove triethylamine hydrochloride, the solvent was then removed, and then ligand L6 (15.15 g) was obtained after separation and purification by column chromatography (eluent: ethyl acetate/n-hexane=1/200 to 1/100), the yield was 30.8%, and the purity was 93.4%.

Preparation of Tetradentate Phosphite Ligand-Nickel Catalyst F 10.7 mmol of tetradentate phosphite ligand L6 and 20 mmol of bis (1,5-cyclooctadiene) nickel were added to 100 mL of toluene under nitrogen atmosphere. Next, the reaction system was mixed and allowed to react at 50° C. for 10 hours. After the reaction was completed, the solvent was removed, and tetradentate phosphite ligand-nickel complex catalyst F was obtained by recrystallization from acetonitrile solvent upon cooling, and the nickel content of catalyst F was 1.16 mmol/g.

Preparation of Adiponitrile

Preparation and analysis were carried out in the same manner as in Example 1 except that catalyst F was used.

28

Example 7

Preparation of Tetradentate Phosphite Ligand L7:

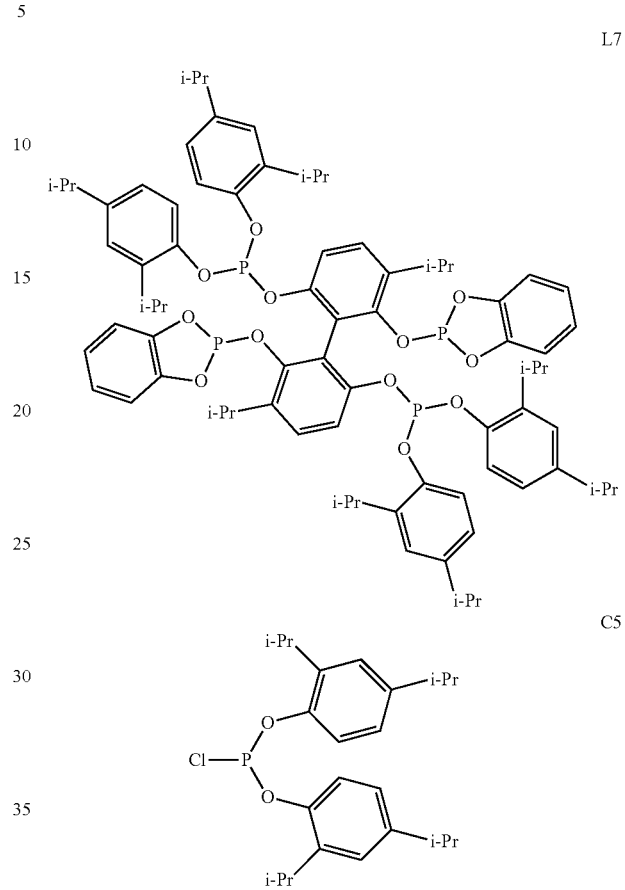

A toluene (200 mL) solution containing 2,2',6,6'-tetrahydroxy-3,3'-diisopropylbiphenyl (9.07 g, 30 mmol) and triethylamine (6.80 g, 67.2 mmol) was added dropwise to a toluene solution containing chlorophosphite C5 (27.78 g, 66 mmol) represented by formula C5 at 5° C. After the addition was completed, the temperature of the reaction system was kept at 5° C., and the reaction was continued for 2 hours. Next, toluene solutions of chlorophosphite C1 (12.51 g, 66 mmol) and triethylamine (6.80 g, 67.2 mmol) were added dropwise to the reaction solution. After the addition was completed, the temperature of the system was kept at 5° C., and the reaction was continued for 2 hours under stirring, and the system was slowly raised to 25° C. and continuously stirred for 4 hours. Subsequently, the reaction solution was filtered to remove triethylamine hydrochloride, the solvent was then removed, and then ligand L7 (8.60 g) was obtained after separation and purification by column chromatography (eluent: ethyl acetate/n-hexane=1/200 to 1/100), the yield was 19.6%, and the purity was 91.8%.

Preparation of Tetradentate Phosphite Ligand-Nickel Catalyst G 10.9 mmol of tetradentate phosphite ligand L7 and 20 mmol of bis (1,5-cyclooctadiene) nickel were added to 100 mL of toluene under nitrogen atmosphere. Next, the reaction system was mixed and allowed to react at 50° C. for 10 hours. After the reaction was completed, the solvent was removed, and tetradentate phosphite ligand-nickel complex catalyst G was obtained by recrystallization from acetonitrile, and the nickel content of catalyst G was 1.25 mmol/g.

Preparation of Adiponitrile

Preparation and analysis were carried out in the same manner as in Example 1 only except that catalyst G was used.

Example 8

Preparation of Tetradentate Phosphite Ligand L8:

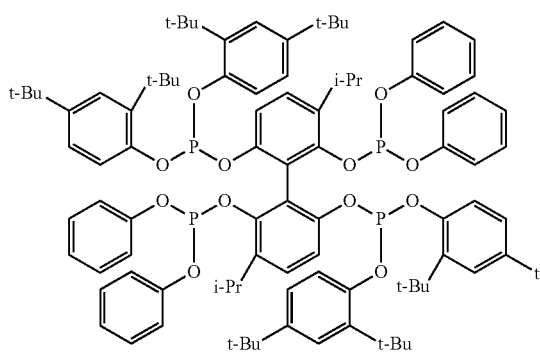

L8

A toluene (200 mL) solution containing 2,2',6,6'-tetrahydroxy-3,3'-diisopropylbiphenyl (9.07 g, 30 mmol) and triethylamine (6.80 g, 67.2 mmol) was added to a toluene solution containing chlorophosphite C4 (31.49 g, 66 mmol) at 5° C. After the addition was completed, the temperature of the reaction system was kept at 5° C., and the reaction was continued for 2 hours. Next, toluene solutions of chlorophosphite C2 (16.67 g, 66 mmol) and triethylamine (6.80 g, 67.2 mmol) were added dropwise to the reaction solution. After the addition was completed, the temperature of the system was kept at 5° C., and the reaction was continued for 2 hours under stirring, and the system was slowly raised to 25° C. and continuously stirred for 4 hours. Subsequently, the reaction solution was filtered to remove triethylamine hydrochloride, the solvent was then removed, and then ligand L8 (13.95 g) was obtained after separation and purification by column chromatography (eluent: ethyl acetate/n-hexane=1/200 to 1/100), the yield was 24.6%, and the purity was 85.4%.

Preparation of Tetradentate Phosphite Ligand-Nickel Catalyst H 11.7 mmol of tetradentate phosphite ligand L8 and 20 mmol of bis (1,5-cyclooctadiene) nickel were added to 100 mL of toluene under a nitrogen atmosphere. Next, the mixture was mixed and reacted at 50° C. for 10 hours. After the reaction was completed, the solvent was removed, and tetradentate phosphite ligand-nickel complex catalyst H was obtained by recrystallization from acetonitrile solvent upon cooling, and the nickel content of catalyst H was 1.10 mmol/g.

Preparation of Adiponitrile

Preparation and analysis were carried out in the same manner as in Example 1 only except that catalyst H was used.

Example 9

Preparation of Tetradentate Phosphite Ligand L9:

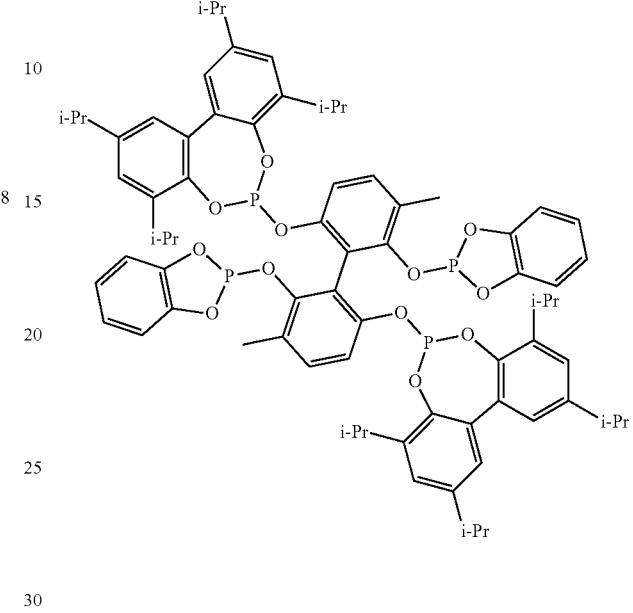

L9

A toluene (200 mL) solution containing 2,2',6,6'-tetrahydroxy-3,3'-dimethylbiphenyl (7.39 g, 30 mmol) and triethylamine (6.80 g, 67.2 mmol) was added dropwise to a toluene solution containing chlorophosphite C3 (27.65 g, 66 mmol) at 5° C. After the addition was completed, the temperature of the reaction system was kept at 5° C., and the reaction was continued for 2 hours. Next, toluene solutions of chlorophosphite C1 (12.51 g, 66 mmol) and triethylamine (6.80 g, 67.2 mmol) were added dropwise to the reaction solution. After the addition was completed, the temperature of the system was kept at 5° C., and the reaction was continued for 2 hours under stirring, and the system was slowly raised to 25° C. and continuously stirred for 4 hours. Subsequently, the reaction solution was filtered to remove triethylamine hydrochloride, the solvent was then removed, and then ligand L9 (15.87 g) was obtained after separation and purification by column chromatography (eluent: ethyl acetate/n-hexane=1/200 to 1/100), the yield was 38.7%, and the purity was 94.2%.

Preparation of Tetradentate Phosphite Ligand-Nickel Catalyst I 10.6 mmol of tetradentate phosphite ligand L9 and 20 mmol of bis (1,5-cyclooctadiene) nickel were added to 100 mL of toluene under a nitrogen atmosphere. Next, the mixture was mixed and reacted at 50° C. for 10 hours. After the reaction was completed, the solvent was removed to directly obtain catalyst I, and the nickel content thereof was 1.26 mmol/g.

Preparation of Adiponitrile

Preparation and analysis were carried out in the same manner as in Example 1 only except that catalyst I was used.

Example 10

Preparation of Tetradentate Phosphite Ligand L10:

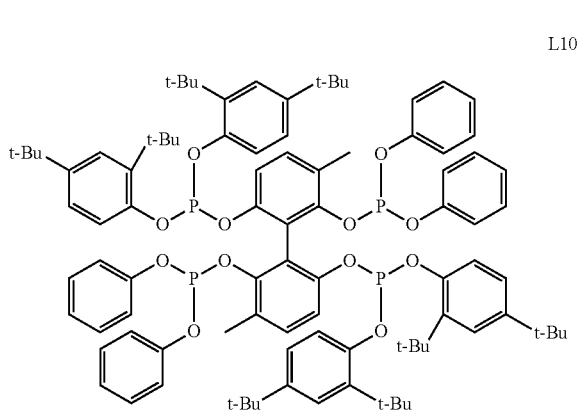 [SMILES: Cc1ccc(OP(Oc2ccc(C(C)(C)C)cc2C(C)(C)C)Oc2ccc(C(C)(C)C)cc2C(C)(C)C)c(-c2c(OP(Oc3ccc(C(C)(C)C)cc3C(C)(C)C)Oc3ccc(C(C)(C)C)cc3C(C)(C)C)ccc(C)c2OP(Oc2ccccc2)Oc2ccccc2)c1OP(Oc1ccccc1)Oc1ccccc1]

A toluene (200 mL) solution containing 2,2',6,6'-tetrahydroxy-3,3'-dimethylbiphenyl (7.39 g, 30 mmol) and triethylamine (6.80 g, 67.2 mmol) was added to a toluene solution containing chlorophosphite C4 (31.49 g, 66 mmol) at 5° C. After the addition was completed, the temperature of the reaction system was kept at 5° C., and the reaction was continued for 2 hours. Next, toluene solutions of chlorophosphite C2 (16.67 g, 66 mmol) and triethylamine (6.80 g, 67.2 mmol) were added dropwise to the reaction solution. After the addition was completed, the temperature of the system was kept at 5° C., and the reaction was continued for 2 hours under stirring, and the system was slowly raised to 25° C. and continuously stirred for 4 hours. Subsequently, the reaction solution was filtered to remove triethylamine hydrochloride, the solvent was then removed, and then ligand L10 (16.36 g) was obtained after separation and purification by column chromatography (eluent: ethyl acetate/n-hexane=1/200 to 1/100), the yield was 29.3%, and the purity was 83.7%.

Preparation of Tetradentate Phosphite Ligand-Nickel Catalyst J 11.9 mmol of tetradentate phosphite ligand L10 and 20 mmol of bis (1,5-cyclooctadiene) nickel were added to 100 mL of toluene under nitrogen atmosphere. Next, the reaction system was mixed and allowed to react at 50° C. for 10 hours. After the reaction was completed, the solvent was removed to directly obtain catalyst J, and the nickel content thereof was 1.11 mmol/g.

Preparation of Adiponitrile

Preparation and analysis were carried out in the same manner as in Example 1 only except that catalyst J was used.

Example 11

Preparation of Tetradentate Phosphite Ligand L11:

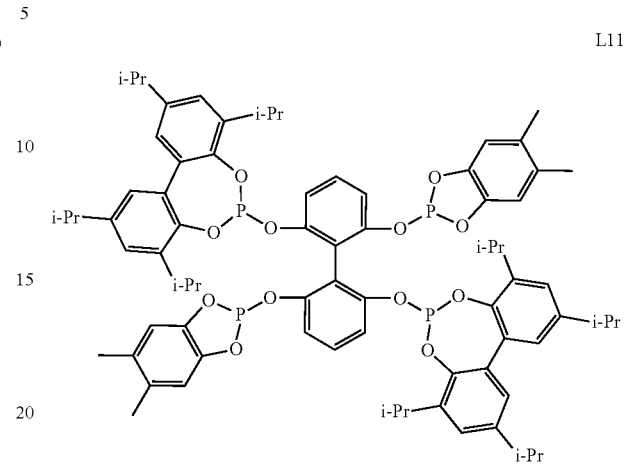

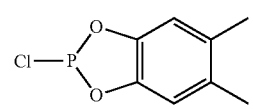

A toluene (200 mL) solution containing 2,2',6,6'-tetrahydroxybiphenyl (6.55 g, 30 mmol) and triethylamine (6.80 g, 67.2 mmol) was added to a toluene solution containing chlorophosphite C3 (27.65 g, 66 mmol) at 5° C. After the addition was completed, the temperature of the reaction system was kept at 5° C., and the reaction was continued for 2 hours. Next, toluene solutions of chlorophosphite C6 (14.36 g, 66 mmol) represented by formula C6 and triethylamine (6.80 g, 67.2 mmol) were added dropwise to the reaction solution. After the addition was completed, the temperature of the system was kept at 5° C., and the reaction was continued for 2 hours under stirring, and the system was slowly raised to 25° C. and continuously stirred for 4 hours. Subsequently, the reaction solution was filtered to remove triethylamine hydrochloride, the solvent was then removed, and then ligand L11 (15.99 g) was obtained after separation and purification by column chromatography (eluent: ethyl acetate/n-hexane=1/200 to 1/100), the yield was 38.2%, and the purity was 94.3%.

Preparation of Tetradentate Phosphite Ligand-Nickel Catalyst K 10.6 mmol of tetradentate phosphite ligand L11 and 20 mmol of bis (1,5-cyclooctadiene) nickel were added to 100 mL of toluene under nitrogen atmosphere. Next, the reaction system was mixed and allowed to react at 50° C. for 10 hours. After the reaction was completed, the solvent was removed, and tetradentate phosphite ligand-nickel complex catalyst K was obtained by recrystallization from acetonitrile solvent upon cooling, and the nickel content of catalyst K was 1.31 mmol/g.

Preparation of Adiponitrile

Preparation and analysis were carried out in the same manner as in Example 1 only except that catalyst K was used.

Example 12

Preparation of Tetradentate Phosphite Ligand L12:

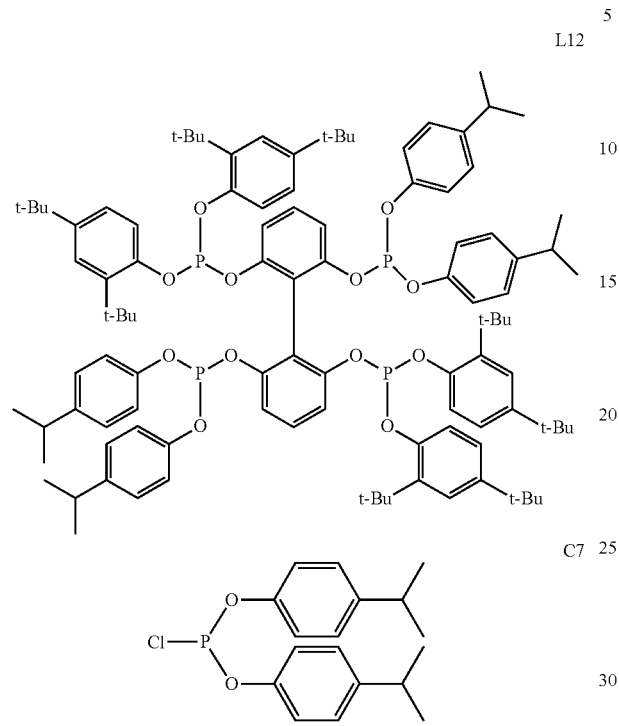

A toluene (200 mL) solution containing 2,2',6,6'-tetrahydroxybiphenyl (6.55 g, 30 mmol) and triethylamine (6.80 g, 67.2 mmol) was added to a toluene solution containing chlorophosphite C4 (31.49 g, 66 mmol) at 5° C. After the addition was completed, the temperature of the reaction system was kept at 5° C., and the reaction was continued for 2 hours. Next, toluene solutions of chlorophosphite formula C7 (22.23 g, 66 mmol) represented by C7 and triethylamine (6.80 g, 67.2 mmol) were added dropwise to the reaction solution. After the addition was completed, the temperature of the system was kept at 5° C., and the reaction was continued for 2 hours under stirring, and the system was slowly raised to 25° C. and continuously stirred for 4 hours. Subsequently, the reaction solution was filtered to remove triethylamine hydrochloride, the solvent was then removed, and then ligand L12 (16.16 g) was obtained after separation and purification by column chromatography (eluent: ethyl acetate/n-hexane=1/200 to 1/100), the yield was 29.5%, and the purity was 93.1%.

Preparation of Tetradentate Phosphite Ligand-Nickel Catalyst L 10.7 mmol of tetradentate phosphite ligand L12 and 20 mmol of bis (1,5-cyclooctadiene) nickel were added to 100 mL of toluene under nitrogen atmosphere. Next, the reaction system was mixed and allowed to react at 50° C. for 10 hours. After the reaction was completed, the solvent was removed, and tetradentate phosphite ligand-nickel complex catalyst L was obtained by recrystallization from acetonitrile solvent upon cooling, and the nickel content of catalyst L was 1.02 mmol/g.

Preparation of Adiponitrile

Preparation and analysis were carried out in the same manner as in Example 1 only except that catalyst L was used.

Example 13

Preparation of Tridentate Phosphite Ligand L13:

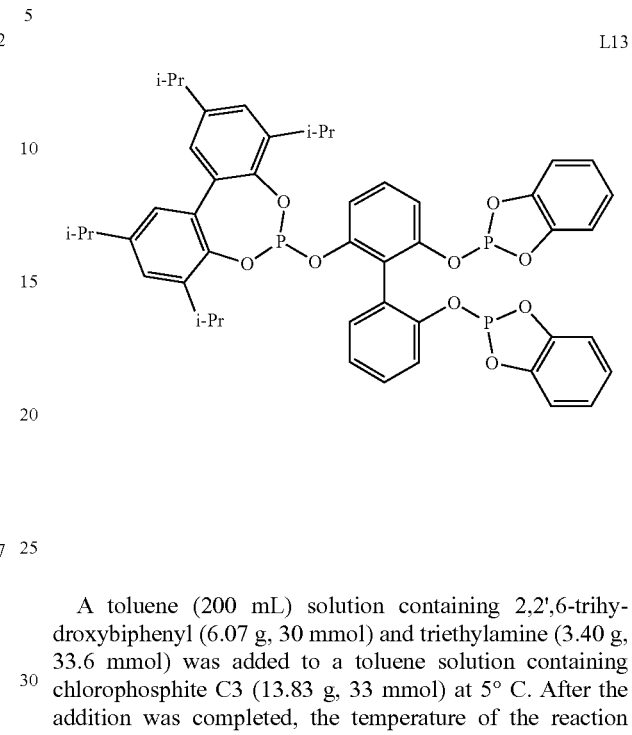

A toluene (200 mL) solution containing 2,2',6-trihydroxybiphenyl (6.07 g, 30 mmol) and triethylamine (3.40 g, 33.6 mmol) was added to a toluene solution containing chlorophosphite C3 (13.83 g, 33 mmol) at 5° C. After the addition was completed, the temperature of the reaction system was kept at 5° C., and the reaction was continued for 2 hours. Next, toluene solutions of chlorophosphite C1 (12.51 g, 66 mmol) and triethylamine (6.80 g, 67.2 mmol) were added dropwise to the reaction solution. After the addition was completed, the temperature of the system was kept at 5° C., and the reaction was continued for 2 hours under stirring, and the system was slowly raised to 25° C. and continuously stirred for 4 hours. Subsequently, the reaction solution was filtered to remove triethylamine hydrochloride, the solvent was then removed, and then ligand L13 (20.96 g) was obtained after separation and purification by column chromatography (eluent: ethyl acetate/n-hexane=1/200 to 1/100), the yield was 75.8%, and the purity was 93.4%.

Preparation of Tridentate Phosphite Ligand-Nickel Catalyst M 21.4 mmol of tetradentate phosphite ligand L13 and 20 mmol of bis (1,5-cyclooctadiene) nickel were added to 100 mL of toluene under nitrogen atmosphere. Next, the reaction system was mixed and allowed to react at 50° C. for 10 hours. After the reaction was completed, the solvent was removed to directly obtain catalyst M, and the nickel content thereof was 0.93 mmol/g.

Preparation of Adiponitrile

Preparation and analysis were carried out in the same manner as in Example 1, wherein the amount (in terms of the mole number of nickel) of the catalyst M used in the primary hydrocyanation reaction was 0.3% of the mole number of starting material BD, and the amount (in terms of the mole number of nickel) of the catalyst M used in the isomerization reaction was 0.3% of the mole number of 2M3BN, and the amount (in terms of the mole number of nickel) of the catalyst M used in the secondary hydrocyanation reaction was 0.6% of the mole number of 3PN.

Example 14

Preparation of Tridentate Phosphite Ligand L14:

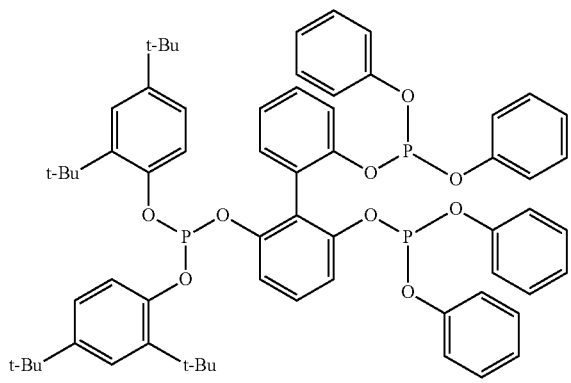

L14

A toluene (200 mL) solution containing 2,2',6-trihydroxybiphenyl (6.07 g, 30 mmol) and triethylamine (3.40 g, 33.6 mmol) was added to a toluene solution containing chlorophosphite C4 (15.75 g, 33 mmol) at 5° C. After the addition was completed, the temperature of the reaction system was kept at 5° C., and the reaction was continued for 2 hours. Next, toluene solutions of chlorophosphite C2 (16.67 g, 66 mmol) and triethylamine (6.80 g, 67.2 mmol) were added dropwise to the reaction solution. After the addition was completed, the temperature of the system was kept at 5° C., and the reaction was continued for 2 hours under stirring, and the system was slowly raised to 25° C. and continuously stirred for 4 hours. Subsequently, the reaction solution was filtered to remove triethylamine hydrochloride, the solvent was then removed, and then ligand L14 (23.1 g) was obtained after separation and purification by column chromatography (eluent: ethyl acetate/n-hexane=1/200 to 1/100), the yield was 66.5%, and the purity was 92.6%.

Preparation of Tridentate Phosphite Ligand-Nickel Catalyst N 21.6 mmol of tetradentate phosphite ligand L14 and 20 mmol of bis (1,5-cyclooctadiene) nickel were added to 100 mL of toluene under nitrogen atmosphere. Next, the reaction system was mixed and allowed to react at 50° C. for 10 hours. After the reaction was completed, the solvent was removed, and tridentate phosphite ligand-nickel complex catalyst N was obtained by recrystallization from acetonitrile solvent upon cooling, and the nickel content of catalyst N was 0.84 mmol/g.

Preparation of Adiponitrile

Preparation and analysis were carried out in the same manner as in Example 1, wherein the amount (in terms of the mole number of nickel) of the catalyst N used in the primary hydrocyanation reaction was 0.3% of the mole number of starting material BD, and the amount (in terms of the mole number of nickel) of the catalyst N used in the isomerization reaction was 0.3% of the mole number of 2M3BN, and the amount (in terms of the mole number of nickel) of the catalyst N used in the secondary hydrocyanation reaction was 0.6% of the mole number of 3PN.

Comparative Example 1

Preparation of Bidentate Phosphite Ligand D1:

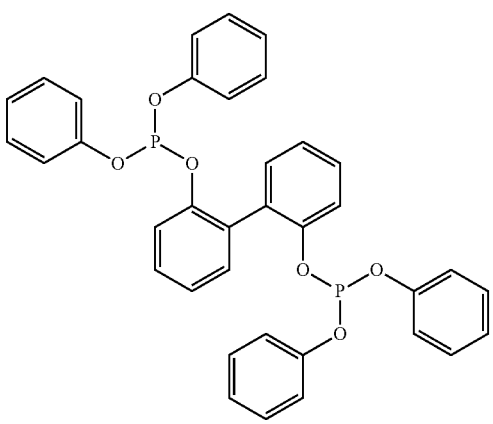

D1

A toluene (100 mL) solution containing 2,2'-dihydroxybiphenyl (4.47 g, 24 mmol) and triethylamine (5.67 g, 56.0 mmol) was added dropwise to a toluene solution containing chlorophosphite C2 (12.63 g, 50 mmol) at 5° C. After the addition was completed, the temperature of the reaction system was kept at 5° C., and the reaction was continued for 2 hours under stirring, and the system was slowly raised to 25° C. and continuously stirred for 4 hours. Subsequently, the reaction solution was filtered to remove triethylamine hydrochloride, the solvent was then removed, and then ligand D1 (13.94 g) was obtained after separation and purification by column chromatography (eluent: ethyl acetate/n-hexane=1/200 to 1/100), the yield was 91.2%, and the purity was 97.1%.

Preparation of Bidentate Phosphite Ligand-Nickel Catalyst Da 20.6 mmol of tetradentate phosphite ligand D1 and 20 mmol of bis (1,5-cyclooctadiene) nickel were added to 100 mL of toluene under nitrogen atmosphere. Next, the reaction system was mixed and allowed to react at 50° C. for 10 hours. After the reaction was completed, the solvent was removed to directly obtain catalyst Da, and the nickel content thereof was 1.22 mmol/g.

Preparation of Adiponitrile

Preparation and analysis were carried out in the same manner as in Example 1, wherein the amount (in terms of the mole number of nickel) of the catalyst Da used in the primary hydrocyanation reaction was 0.4% of the mole number of starting material BD, and the amount (in terms of the mole number of nickel) of the catalyst Da used in the isomerization reaction was 0.4% of the mole number of 2M3BN, and the amount (in terms of the mole number of nickel) of the catalyst Da used in the secondary hydrocyanation reaction was 0.6% of the mole number of 3PN.

Comparative Example 2

Preparation of Bidentate Phosphite Ligand D2:

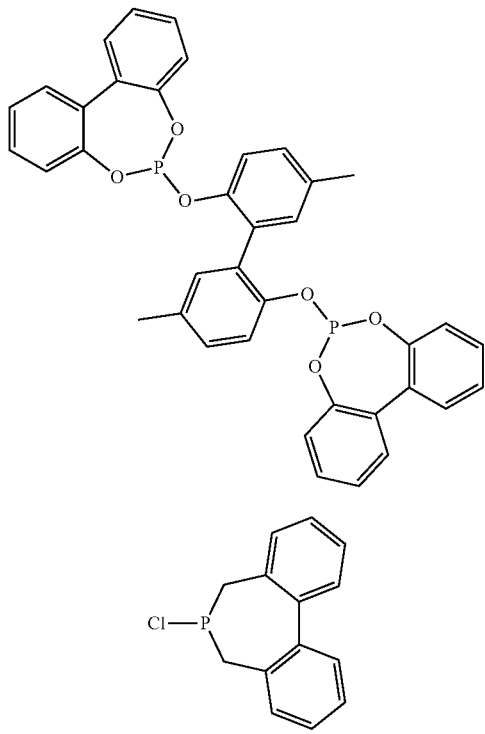

A toluene (100 mL) solution containing 2,2'-dihydroxy-5,5'-dimethylbiphenyl (5.14 g, 24 mmol) and triethylamine (5.67 g, 56.0 mmol) was added to a toluene solution containing chlorophosphite C8 (12.53 g, 50 mmol) represented by formula C8 at 5° C. After the addition was completed, the temperature of the reaction system was kept at 5° C., and the reaction was continued for 2 hours under stirring, and the system was slowly raised to 25° C. and continuously stirred for 4 hours. Subsequently, the reaction solution was filtered to remove triethylamine hydrochloride, the solvent was then removed, and then ligand D2 (13.94 g) was obtained after separation and purification by column chromatography (eluent: ethyl acetate/n-hexane=1/200 to 1/100), the yield was 84.5%, and the purity was 93.5%.

Preparation of Bidentate Phosphite Ligand-Nickel Catalyst Db 21.4 mmol of tetradentate phosphite ligand D2 and 20 mmol of bis (1,5-cyclooctadiene) nickel were added to 100 mL of toluene under nitrogen atmosphere. Next, the reaction system was mixed and allowed to react at 50° C. for 10 hours. After the reaction was completed, the solvent was removed, and bidentate phosphite ligand-nickel complex catalyst Db was obtained by recrystallizztion from acetonitrile solvent upon cooling, and the nickel content of the catalyst Db was 1.19 mmol/g.

Preparation of Adiponitrile

Preparation and analysis were carried out in the same manner as in Example 1, wherein the amount (in terms of the mole number of nickel) of the catalyst Db used in the primary hydrocyanation reaction was 0.4% of the mole number of starting material BD, and the amount (in terms of the mole number of nickel) of the catalyst Db used in the isomerization reaction was 0.4% of the mole number of 2M3BN, and the amount (in terms of the mole number of nickel) of the catalyst Db used in the secondary hydrocyanation reaction was 0.6% of the mole number of 3PN.

Comparative Example 3

Preparation of Bidentate Phosphite Ligand D3:

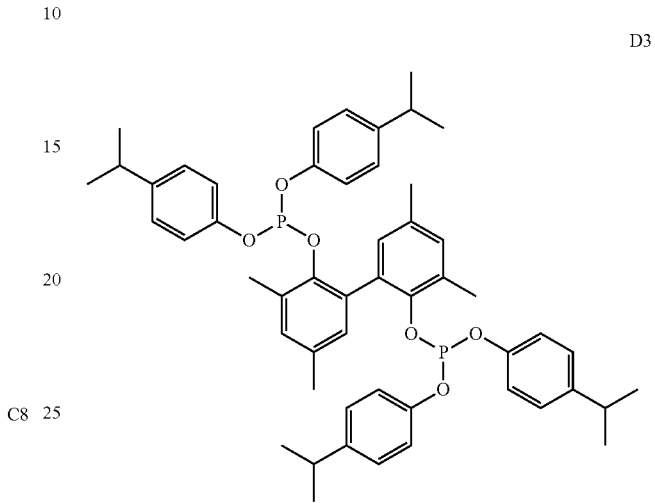

A toluene (100 mL) solution containing 2,2'-dihydroxy-3,3',5,5'-tetramethylbiphenyl (5.82 g, 24 mmol) and triethylamine (5.67 g, 56.0 mmol) was added to a toluene solution containing chlorophosphite C7 (16.84 g, 50 mmol) at 5° C. After the addition was completed, the temperature of the reaction system was kept at 5° C., and the reaction was continued for 2 hours under stirring, and the system was slowly raised to 25° C. and continuously stirred for 4 hours. Subsequently, the reaction solution was filtered to remove triethylamine hydrochloride, the solvent was then removed, and then ligand D3 (17.83 g) was obtained after separation and purification by column chromatography (eluent: ethyl acetate/n-hexane=1/200 to 1/100), the yield was 83.9%, and the purity was 95.2%.

Preparation of Bidentate Phosphite Ligand-Nickel Catalyst Dc 21.0 mmol of tetradentate phosphite ligand D3 and 20 mmol of bis (1,5-cyclooctadiene) nickel were added to 100 mL of toluene under a nitrogen atmosphere. Next, the mixture was mixed and reacted at 50° C. for 10 hours. After the reaction was completed, the solvent was removed, and bidentate phosphite ligand-nickel complex catalyst Dc was obtained by recrystallization acetonitrile solvent upon cooling, and the nickel content of catalyst Dc was 1.03 mmol/g.

Preparation of Adiponitrile

Preparation and analysis were carried out in the same manner as in Example 1, wherein the amount (in terms of the mole number of nickel) of the catalyst Dc used in the primary hydrocyanation reaction was 0.4% of the mole number of starting material BD, and the amount (in terms of the mole number of nickel) of the catalyst Dc used in the isomerization reaction was 0.4% of the mole number of 2M3BN, and the amount (in terms of the mole number of nickel) of that catalyst Dc used in the secondary hydrocyanation reaction was 0.6% of the mole number of 3PN.

The results of the synthesis of the multidentate phosphite ligands and multidentate phosphite ligand-nickel catalysts, and the results of the catalytic synthesis of adiponitrile and the intermediates thereof involved in the above examples are summarized in Tables 2 and 3, respectively.

different structure A1 from A4, a different structure A2 from A3, the same structure A1 as A2 or A3, and the same structure A4 as A3 or A2 in general formula (I). The linear

TABLE 2

Summary of results for the synthesis of multidentate phosphite ligands and multidentate phosphite ligand-nickel catalysts

| Phosphite ligand No. | Molecular weight of phosphite ligand (g/mol) | Preparation of phosphite ligand | | | | | | Phosphite ligand-nickel catalyst | | | |
|---|---|---|---|---|---|---|---|---|---|---|---|
| | | Amount of chlorophosphite (mmol) | Amount of diphenol (mmol) | Amount of triethylamine (mmol) | Mass of phosphite ligand (g) | Yield of ligand (%) | Purity of phosphite ligand (%) | Catalyst No. | Ni source | Molar ratio of phosphite ligand to Ni | Ni content (mmol/g) |
| L1 | 770.4 | 100 | 20 | 112 | 13.72 | 86.1 | 96.7 | A | Ni (COD)$_2$ | 1.03:2 | 1.82 |
| L2 | 1082.9 | 100 | 20 | 112 | 18.57 | 84.3 | 98.3 | B | Ni (COD)$_2$ | 1.02:2 | 1.60 |
| L3 | 1748.1 | 100 | 20 | 112 | 22.30 | 59.5 | 93.3 | C | Ni (COD)$_2$ | 1.07:2 | 1.02 |
| L4 | 1980.6 | 100 | 20 | 112 | 19.74 | 42.4 | 85.1 | D | Ni (COD)$_2$ | 1.18:2 | 0.91 |
| L5 | 1259.3 | 66 + 66 | 30 | 134.4 | 18.54 | 42.3 | 86.2 | E | Ni (COD)$_2$ | 1.16:2 | 1.33 |
| L6 | 1531.7 | 66 + 66 | 30 | 134.4 | 15.15 | 30.8 | 93.4 | F | Ni (COD)$_2$ | 1.07:2 | 1.16 |
| L7 | 1347.5 | 66 + 66 | 30 | 134.4 | 8.60 | 19.6 | 91.8 | G | Ni (COD)$_2$ | 1.09:2 | 1.25 |
| L8 | 1613.9 | 66 + 66 | 30 | 134.4 | 13.95 | 24.6 | 85.4 | H | Ni (COD)$_2$ | 1.17:2 | 1.10 |
| L9 | 1287.3 | 66 + 66 | 30 | 134.4 | 15.87 | 38.7 | 94.2 | I | Ni (COD)$_2$ | 1.06:2 | 1.26 |
| L10 | 1557.8 | 66 + 66 | 30 | 134.4 | 16.36 | 29.3 | 83.7 | J | Ni (COD)$_2$ | 1.19:2 | 1.11 |
| L11 | 1315.4 | 66 + 66 | 30 | 134.4 | 15.99 | 38.2 | 94.3 | K | Ni (COD)$_2$ | 1.06:2 | 1.31 |
| L12 | 1700.1 | 66 + 66 | 30 | 134.4 | 16.16 | 29.5 | 93.1 | L | Ni (COD)$_2$ | 1.07:2 | 1.02 |
| L13 | 860.8 | 33 + 66 | 30 | 100.8 | 20.96 | 75.8 | 93.4 | M | Ni (COD)$_2$ | 2.14:2 | 0.93 |
| L14 | 1075.1 | 33 + 66 | 30 | 100.8 | 23.16 | 66.5 | 92.6 | N | Ni (COD)$_2$ | 2.16:2 | 0.84 |
| D1 | 618.5 | 50 | 24 | 56.0 | 13.94 | 91.2 | 97.1 | Da | Ni (COD)$_2$ | 2.06:2 | 1.22 |
| D2 | 642.6 | 50 | 24 | 56.0 | 13.94 | 84.5 | 93.5 | Db | Ni (COD)$_2$ | 2.14:2 | 1.19 |
| D3 | 843.0 | 50 | 24 | 56.0 | 17.83 | 83.9 | 95.2 | Dc | Ni (COD)$_2$ | 2.10:2 | 1.03 |

TABLE 3

Summary of results for the catalytic synthesis of adiponitrile by multidentate phosphite ligand-nickel catalysts and the intermediates thereof

| | Catalyst | Primary hydrocyanation | | | Isomerization | | Secondary hydrocyanation | |
|---|---|---|---|---|---|---|---|---|
| | | HCN conversion (%) | 3PN + 2M3BN selectivity (%) | 3PN/ 2M3BN | 2M3BN conversion (%) | 3PN selectivity (%) | HCN conversion (%) | ADN selectivity (%) |
| Example 1 | A | >99.9 | 96.5 | 72.3/27.7 | 93.2 | 95.0 | >99.9 | 83.1 |
| Example 2 | B | >99.9 | 96.0 | 77.6/22.4 | 94.0 | 95.2 | >99.9 | 83.3 |
| Example 3 | C | >99.9 | 96.2 | 78.4/21.6 | 94.0 | 95.6 | 99.9 | 84.8 |
| Example 4 | D | 99.2 | 95.1 | 78.8/21.2 | 81.3 | 96.0 | 99.0 | 85.5 |
| Example 5 | E | >99.9 | 96.4 | 89.1/10.9 | 96.0 | 96.3 | >99.9 | 87.2 |
| Example 6 | F | >99.9 | 95.2 | 83.8/16.2 | 86.3 | 96.0 | >99.9 | 87.0 |
| Example 7 | G | >99.9 | 97.4 | 92.2/7.8 | 97.3 | 96.9 | >99.9 | 94.2 |
| Example 8 | H | >99.9 | 96.2 | 90.5/9.5 | 96.3 | 96.3 | >99.9 | 93.4 |
| Example 9 | I | >99.9 | 97.4 | 93.6/6.4 | 97.3 | 97.2 | >99.9 | 93.5 |
| Example 10 | J | >99.9 | 96.2 | 89.3/10.7 | 97.5 | 96.8 | >99.9 | 92.9 |
| Example 11 | K | >99.9 | 96.0 | 80.8/19.2 | 97.0 | 96.7 | >99.9 | 87.3 |
| Example 12 | L | >99.9 | 97.1 | 81.3/18.7 | 98.0 | 95.2 | >99.9 | 88.3 |
| Example 13 | M | >99.9 | 96.5 | 87.4/12.6 | 98.3 | 97.0 | >99.9 | 86.3 |
| Example 14 | N | >99.9 | 96.7 | 86.9/13.1 | 97.3 | 97.2 | >99.9 | 90.1 |
| Comparative example 1 | Da | >99.9 | 97.8 | 70.2/29.8 | 97.0 | 92.3 | >99.9 | 81.7 |
| Comparative example 2 | Db | >99.9 | 96.0 | 82.1/17.9 | 94.3 | 94.5 | >99.9 | 86.9 |
| Comparative example 3 | Dc | >99.9 | 96.5 | 81.3/18.7 | 94.8 | 96.0 | >99.9 | 86.6 |

It can be seen from above Table 3 that in Examples 1 to 14 of the present disclosure, by using the multidentate phosphite ligand in the catalyst used for preparing adiponitrile, the linear selectivity for the product adiponitrile obtained is higher and the amount of catalyst (in terms of the mole number of nickel) used is smaller.

In particular, in Examples 5 to 12, the tetradentate phosphite ligands are formed from two chlorophosphites, that is, the tetradentate phosphite ligand is a compound having a selectivity for the product thus obtained is higher, and the amount of catalyst (in terms of the mole number of nickel) used is smaller.

Bidentate phosphite ligands were used for the catalysts of Comparative Examples 1 to 3, and compared with Examples 1 to 12 of the present disclosure, the linear selectivity for the product is low, and the mass amount of the catalyst (in terms of nickel) used is large.

Example 15 Investigation of Effects of the Amount of Phosphite Ligand-Nickel Catalyst on the Preparation of Adiponitrile Preparation and analysis of adiponitrile were carried out in the same manner as in Example 1, and the amount of the catalyst to be used was adjusted, wherein the molar percentage of the catalyst (in terms of the mole number of nickel) to the starting material BD in the primary hydrocyanation reaction, the molar percentage of the catalyst (in terms of the mole number of nickel) to 2M3BN in the isomerization reaction, and the molar percentage of the catalyst (in terms of the mole number of nickel) to 3PN in the secondary hydrocyanation were shown in Table 4 below. The specific experimental results are summarized in Table 4.

Example 16 Test of Water Resistance Stability of Ligand L7 in Example 6 and Ligand D3 in Comparative Example 3

1.0 g of ligand L7 and D3 samples were respectively weighed and dissolved in 3-pentenenitrile solution (20 mL) with a water content of 500 ppm under the protection of dry high-purity nitrogen and stored at 50° C. The change in the content (mass percent) of the ligand with time was determined by high performance liquid chromatography (HPLC). The specific experimental results were shown in Table 5.

TABLE 4

Effect of the amount of the catalyst on hydrocyanation and isomerization reaction

| | Primary hydrocyanation | | | Isomerization | | | Secondary hydrocyanation | | |
|---|---|---|---|---|---|---|---|---|---|
| Catalyst | HCN conversion (%) | 3PN + 2M3BN selectivity (%) | Amount of catalyst (mol %) | 2M3BN conversion (%) | 3PN selectivity (%) | Amount of catalyst (mol %) | HCN conversion (%) | ADN selectivity (%) | Amount of catalyst (mol %) |
| E | >99.9 | 96.4 | 0.2 | 96.0 | 96.3 | 0.2 | >99.9 | 87.2 | 0.3 |
| E | >99.9 | 96.5 | 0.12 | 95.7 | 96.3 | 0.12 | >99.9 | 87.2 | 0.18 |
| G | >99.9 | 97.4 | 0.2 | 97.3 | 96.9 | 0.2 | >99.9 | 94.2 | 0.3 |
| G | >99.9 | 97.4 | 0.12 | 97.3 | 97.0 | 0.12 | >99.9 | 94.2 | 0.18 |
| G | >99.9 | 97.4 | 0.10 | 97.0 | 96.9 | 0.10 | >99.9 | 94.2 | 0.15 |
| I | >99.9 | 97.4 | 0.2 | 97.3 | 97.2 | 0.2 | >99.9 | 93.5 | 0.3 |
| I | >99.9 | 97.4 | 0.12 | 97.1 | 97.3 | 0.12 | >99.9 | 93.5 | 0.18 |
| I | >99.9 | 97.4 | 0.10 | 97.1 | 97.3 | 0.10 | >99.9 | 93.5 | 0.15 |
| Db | >99.9 | 96.0 | 0.4 | 94.3 | 94.5 | 0.4 | 82.1 | >99.9 | 0.6 |
| Db | 99.8 | 95.8 | 0.2 | 86.3 | 94.5 | 0.2 | 82.1 | 98.7 | 0.3 |
| Dc | >99.9 | 96.5 | 0.4 | 94.8 | 96.0 | 0.4 | 83.7 | >99.9 | 0.6 |
| Dc | 99.7 | 96.2 | 0.2 | 84.7 | 96.0 | 0.2 | 82.1 | 98.9 | 0.3 |

It can be seen from the above table that for the catalysts E, G and I prepared and obtained from tetradentate phosphite ligands, the amount of catalyst used in the three steps of the primary hydrocyanation, isomerization, and secondary hydrocyanation is reduced from 0.2%/0.2%/0.3% to 0.12%/0.12%/0.18%, and the effect of the reaction is still stable. For catalysts G and I, the conversion and selectivity of the first hydrocyanation, isomerization, and the second hydrocyanation are maintained at the same level with the amount of the catalyst reduced to 0.10%/0.10%/0.15%. Similarly, when the amount of the bidentate phosphite-nickel catalysts Db and Dc is reduced to 0.2%/0.2%/0.3%, the conversion of the three steps of reactions is significantly reduced, and the residual amount of hydrocyanic acid is significantly increased.

The above results show that the multidentate phosphite-nickel catalyst has higher catalytic activity and a lower amount used in the reaction process compared with the bidentate phosphite-nickel catalyst.

TABLE 5

Test results of water resistance stability of ligands L7 and D3

| | Content of ligand and other related impurities/% | | | | | | | | |
|---|---|---|---|---|---|---|---|---|---|
| Time/h | L7 | L7-1 | L7-2 | L7-3 | L7-4 | D3 | D3-1 | D3-2 | D3-3 |
| 0 | 91.8 | 0.6 | 2.0 | 5.3 | 0.3 | 95.2 | 0.4 | 4.2 | 0.2 |
| 6 | 91.6 | 0.6 | 2.1 | 4.8 | 0.9 | 95.0 | 0.4 | 3.2 | 1.4 |
| 12 | 91.6 | 0.7 | 2.1 | 4.0 | 1.6 | 94.7 | 0.3 | 2.0 | 3 |
| 18 | 91.5 | 0.4 | 1.8 | 3.1 | 3.2 | 94.0 | 0.5 | 1.1 | 4.4 |
| 24 | 91.2 | 0.5 | 2.0 | 2.1 | 4.2 | 93.0 | 0.5 | 0.3 | 6.2 |
| 48 | 90.7 | 0.5 | 1.7 | 1.0 | 6.1 | 90.5 | 0.3 | 0.2 | 9 |
| 72 | 89.9 | 0.4 | 1.5 | 0.2 | 8 | 86.2 | 0.2 | <0.1 | 13.6 |
| 96 | 88.7 | 0.4 | 1.5 | <0.1 | 9.4 | 82.2 | 0.2 | <0.1 | 17.6 |

In the above Table 5, other related impurities included in the ligand L7 sample are L7-1, L7-2, L7-3, and L7-4 respectively, and other related impurities included in the ligand D3 sample are D3-1, D3-2, and D3-3 respectively, wherein, L7-3 and D3-2 are mainly generated in the synthesis process of ligand, and other substances are obtained by hydrolysis reaction of ligands and the like.

Reaction Formula 1 Hydrolysis Side Reactions of Related Substances in the Ligand L7 Sample
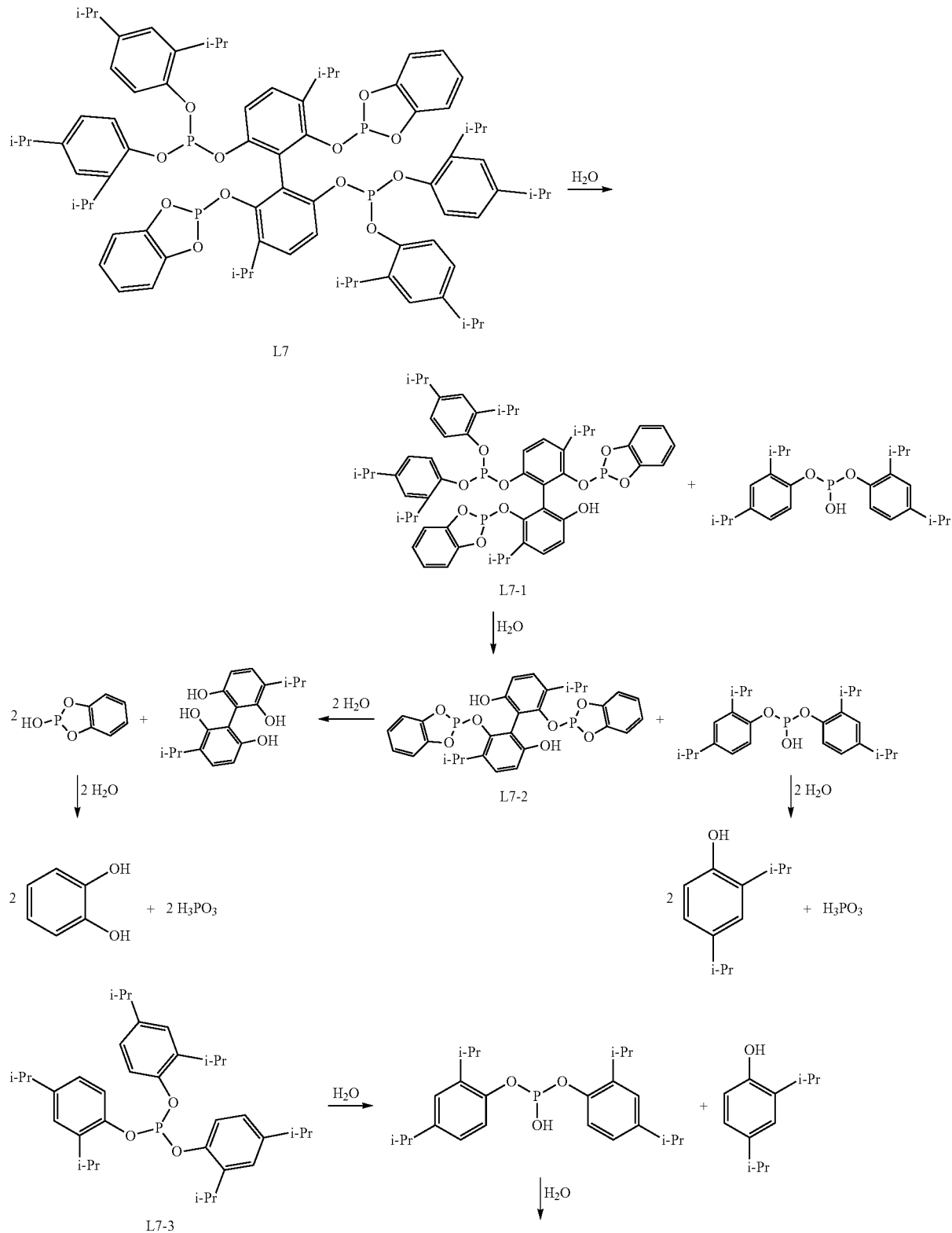

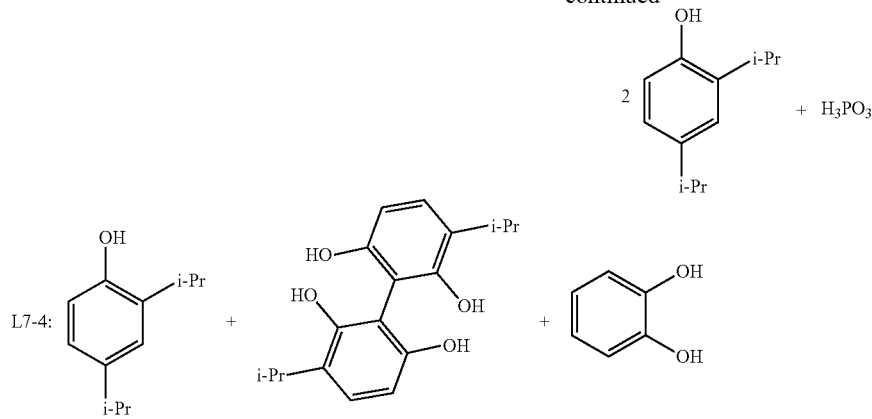
Reaction Formula 2 Hydrolysis Side Reactions of Related Substances in the Ligand D3 Sample
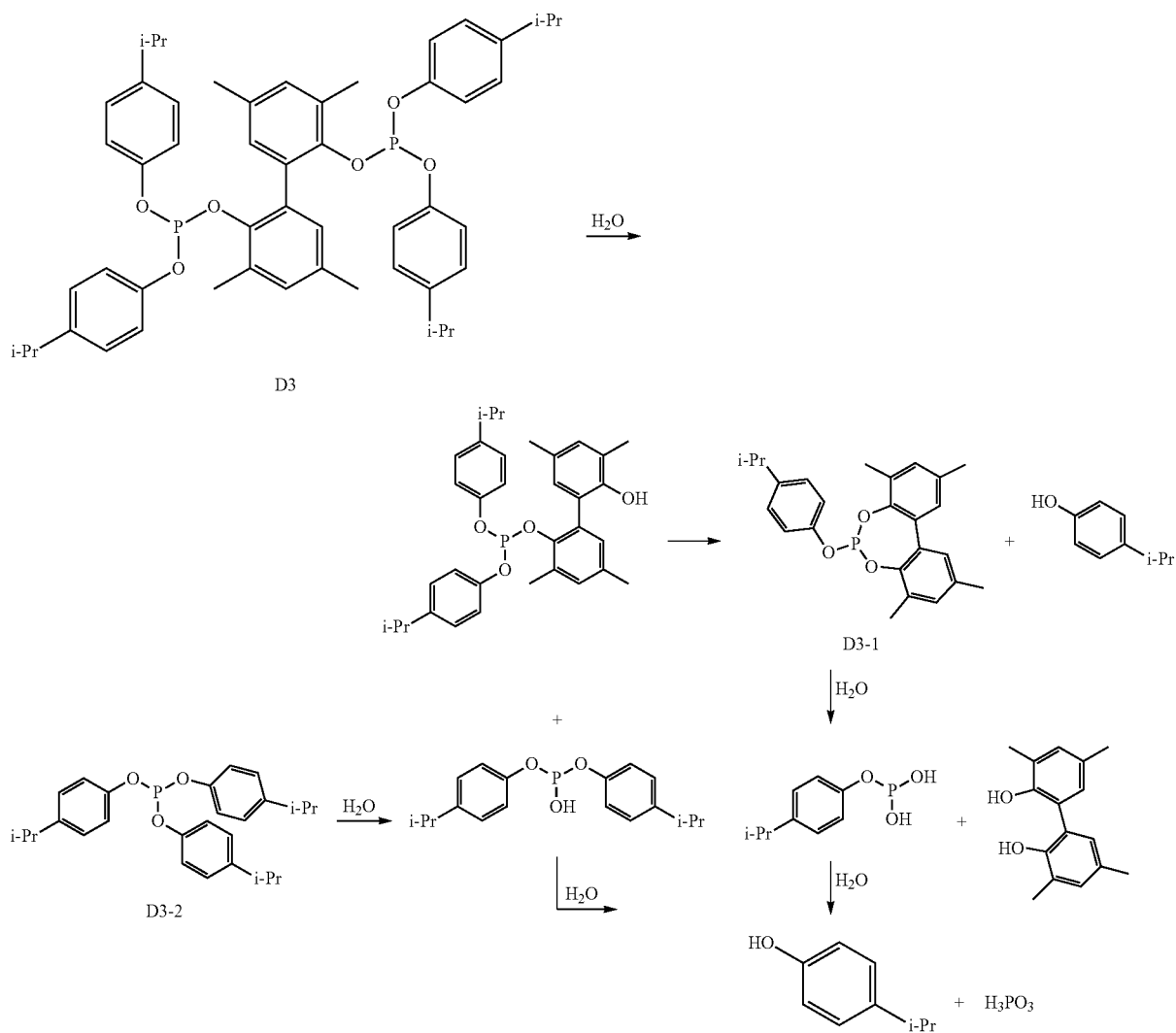

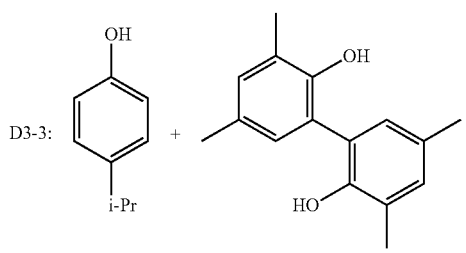

D3-3:

It can be seen from Table 5 that the stability of tetradentate phosphite ligand L7 to water is better than that of bidentate phosphite ligand D3 under the same conditions. Tetradentate phosphite ligand L7 shows quite good water resistance in the first 48 hours, and the content of the tetradentate phosphite ligand L7 only decreased by 1.1%. After 48 hours, the acidity of the ligand solution environment was enhanced due to the continuous accumulation of the hydrolysis products, resulting in phenomenon of autocatalytic hydrolysis. From 48 to 96 hours, the ligand content decreased from 90.7% to 88.7%. By comparison, it can be found that the content of bidentate phosphite ligand D3 decreased from 95.2% to 90.5% in the first 48 hours, and the content of the ligand continued to decrease to 82.2% after another 48 hours.

In order to further compare the water resistance of the tetradentate ligand and the bidentate ligand, the inventors dissolved the tetradentate phosphite ligand L7 and the bidentate phosphite ligand D3 together in a 3-pentenenitrile solution with a water content of 500 ppm, and observed the change of the content of the two ligands with time. The experimental method are as follows:

1.0 g of each sample of ligand L7 and D3 were respectively weighed and dissolved together in a 3-pentenenitrile solution (40 mL) with a water content of 500 ppm under the protection of dry high-purity nitrogen and stored at 50° C. The change in the content of the ligand with time was determined by high performance liquid chromatography (HPLC). The specific experimental results are shown in Table 6.

TABLE 6

Test results of water resistance stability of the mixed solution of ligand L7 and

| | Ligand and hydrolysis by-product content/% | | | | | | | |
|---|---|---|---|---|---|---|---|---|
| Time/h | L7 | L7-1 | L7-2 | L7-3 | D3 | D3-1 | D3-2 | L7-4 + D3-3 |
| 0 | 46.0 | 0.3 | 1.0 | 2.7 | 47.4 | 0.2 | 2.1 | 0.3 |
| 6 | 46.0 | 0.3 | 1.1 | 2.1 | 47.4 | 0.2 | 1.4 | 1.5 |
| 12 | 46.0 | 0.3 | 1.1 | 1.6 | 47.2 | 0.2 | 1.0 | 2.6 |
| 18 | 46.0 | 0.4 | 1.2 | 1.0 | 46.9 | 0.3 | 0.3 | 3.9 |
| 24 | 46.0 | 0.3 | 1.2 | 0.3 | 46.5 | 0.3 | <0.1 | 5.4 |
| 48 | 45.9 | 0.3 | 1.1 | <0.1 | 45.1 | 0.4 | <0.1 | 7.2 |
| 72 | 45.7 | <0.1 | 1.2 | <0.1 | 42.8 | 0.5 | <0.1 | 9.8 |
| 96 | 45.3 | <0.1 | 1.4 | <0.1 | 40.2 | 0.5 | <0.1 | 12.6 |

It can be seen from Table 6 that tetradentate phosphite ligand L7 shows better water resistance when stored at 50° C. for 96 hours, and the content of the tetradentate ligand decreases from 46.0% to 45.3% after 96 hours. However, the content of the bidentate phosphite ligand D3 decreases from 47.4% to 40.2% within 96 hours.

It can be seen from the results of Tables 5 and 6 above, that the multidentate phosphite ligand of the present disclosure is better in water resistance than the bidentate phosphite ligands of the prior art. Therefore, the hydrolysis loss of the multidentate phosphite ligand in the recycling and reusing process may be reduced, the consumption of the ligand and the catalyst may be reduced, and the production cost of adiponitrile is reduced.

What is claimed is:

1. A method of catalytic synthesis of adiponitrile using a multidentate phosphite ligand, wherein the multidentate phosphite ligand is a compound represented by a following general formula (I), the method comprising:
    subjecting butadiene and hydrocyanic acid to a primary hydrocyanation reaction in the presence of a first catalyst;
    subjecting a branched mononitrile mixture to an isomerization reaction of branched mononitriles in a presence of a second catalyst, wherein the branched mononitrile mixture is separated from a product obtained in the primary hydrocyanation reaction; and
    subjecting a linear mononitrile mixture and hydrocyanic acid to a secondary hydrocyanation reaction in the presence of a third catalyst and a promoter to obtain a product containing adiponitrile, wherein the linear mononitrile mixture is separated from the products obtained in the primary hydrocyanation reaction and the isomerization reaction;
    wherein the first catalyst, the second catalyst, and the third catalyst are identical or different, and each of the catalysts comprises a phosphite ligand-zero-valent nickel complex formed of a nickel precursor and the multidentate phosphite ligand:

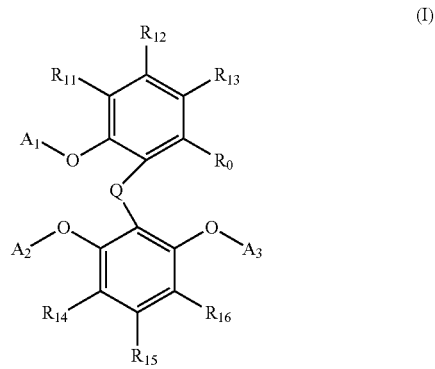

(I)

in formula (1), $R_0$ is —O-$A_4$, H, an $C_{1\text{-}6}$ alkyl group, a substituted or unsubstituted $C_{3\text{-}10}$ cycloalkyl group, or a substituted or unsubstituted $C_{6\text{-}20}$ aryl group;

$R_{11}$ to $R_{16}$ are identical to or different from each other, and each independently represents hydrogen, an $C_{1\text{-}6}$ alkyl group, a substituted or unsubstituted $C_{3\sim10}$ cycloalkyl group, or a substituted or unsubstituted $C_{6\sim20}$ aryl group;

$A_1$, $A_2$, $A_3$, and $A_4$ are identical to or different from each other, and each independently is

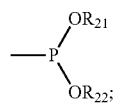

each of $R_{21}$ and each of $R_{22}$ are identical to or different from each other, and each of $R_{21}$ and each of $R_{22}$ is independently H, a substituted or unsubstituted $C_{1\sim6}$ alkyl group, a substituted or unsubstituted $C_{3\sim10}$ cycloalkyl group, a $C_{1\sim6}$ acyl group, or a substituted or unsubstituted $C_{6\sim20}$ aryl group; and $R_{21}$ and $R_{22}$ may bond to form a ring via a single bond, an $C_{1\sim6}$ alkylene group, a phenylene group, or a $C_{1\sim6}$ alkyl substituted phenylene group;

Q is a single bond, an $C_{1\sim3}$ alkylene group, an oxygen atom, a nitrogen atom, or an $C_{1\sim3}$ alkylene group containing an oxygen atom or a nitrogen atom.

2. The method according to claim 1, wherein structures $A_1$, $A_2$, $A_3$, and $A_4$ in general formula (I) are identical to or different from each other and are each independently one of following structures:

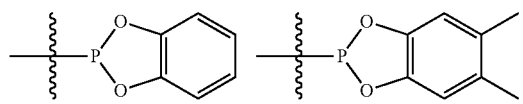

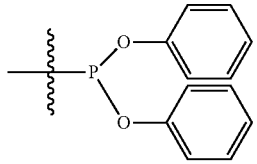

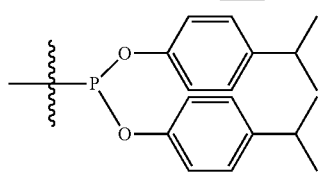

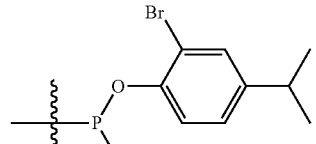

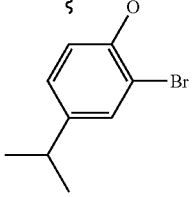

-continued

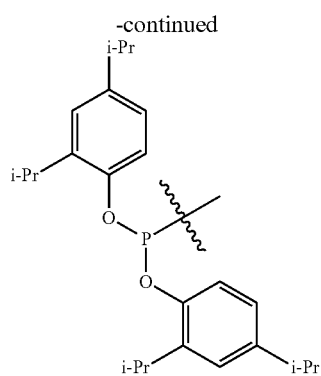

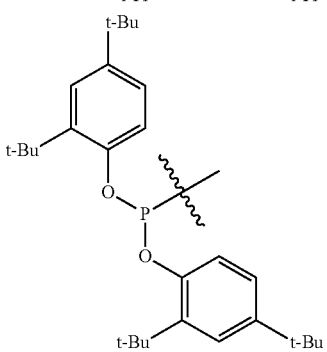

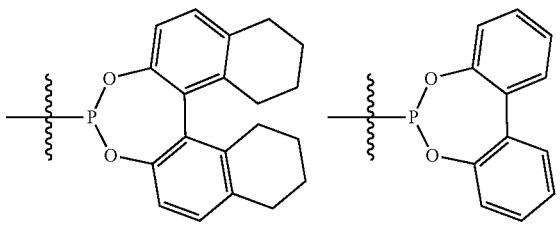

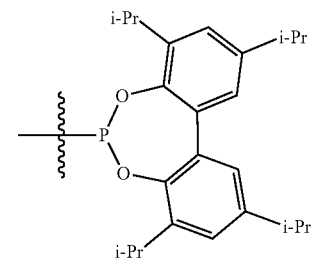

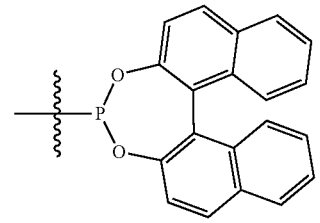

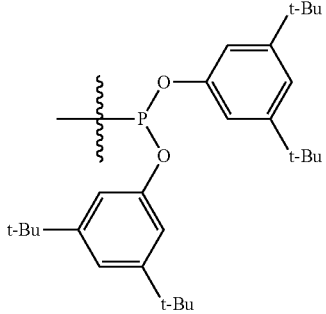

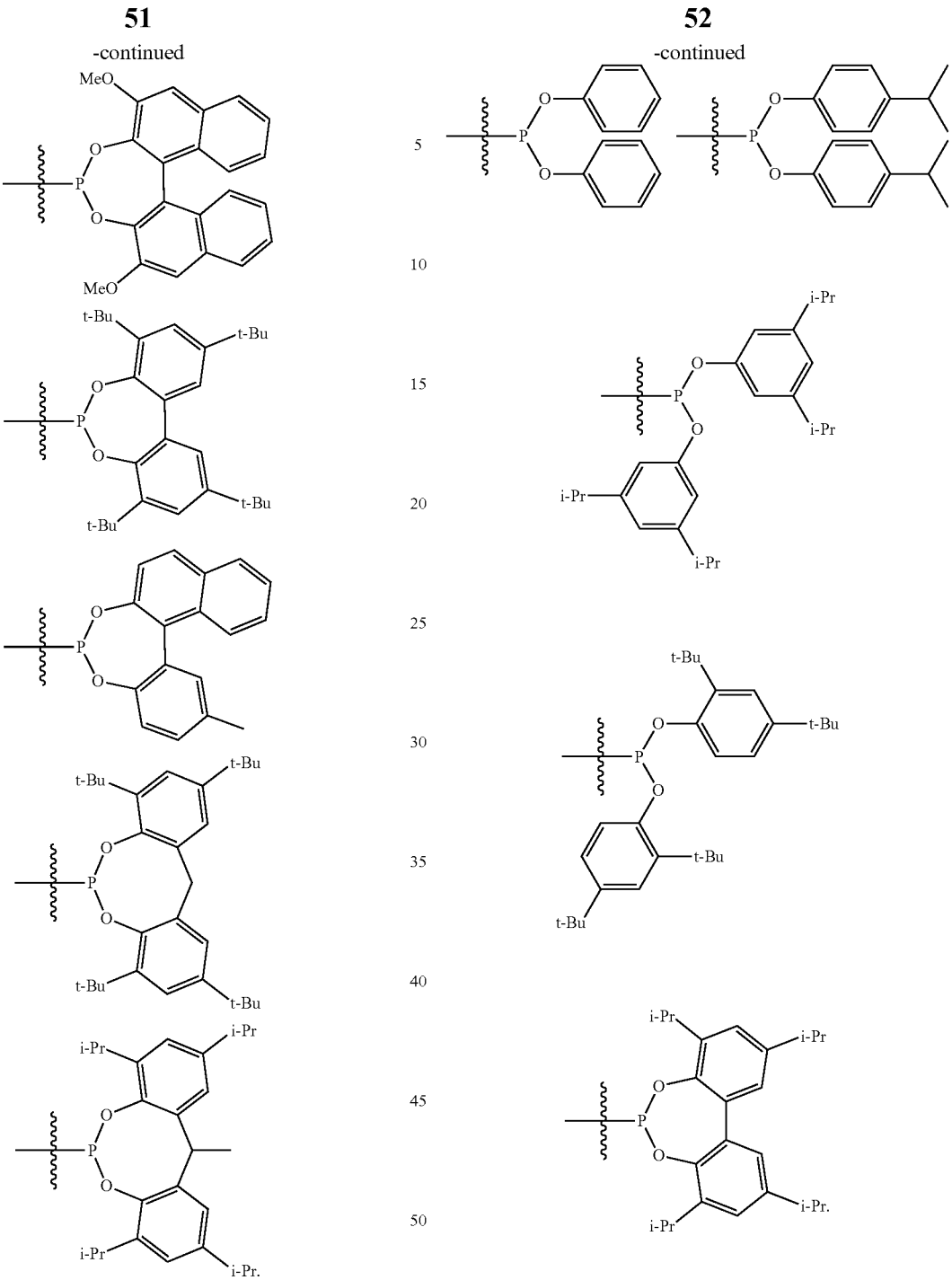

3. The method according to claim 1, wherein structures $A_1$, $A_2$, $A_3$, and $A_4$ in general formula (I) are each independently one of following structures:

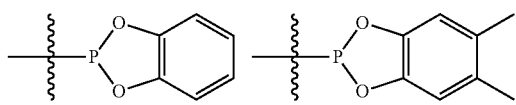

4. The method according to claim 1, wherein at least two of structures $A_1$, $A_2$, $A_3$, and $A_4$ in general formula (I) are different.

5. The method according to claim 1, wherein, in general formula (1), structure $A_1$ is different from structure $A_4$, structure $A_2$ is different from structure $A_3$, structure $A_1$ is identical to structure $A_2$ or $A_3$, and structure $A_4$ is identical to structure $A_3$ or $A_2$.

6. The method according to claim 1, wherein a method for preparing the multidentate phosphite ligand comprises:

reacting a compound represented by the following general formula (II) and at least one halophosphite represented by the general formula (III) with triethylamine in the presence of an organic solvent,

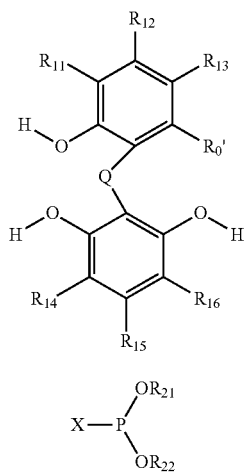 (II)

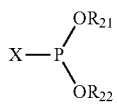 (III)

wherein $R_0'$ represents —OH, H, an $C_{1\sim6}$ alkyl group, a substituted or unsubstituted $C_{3\sim10}$ cycloalkyl group, or a substituted or unsubstituted $C_{6\sim20}$ aryl group;

$R_{11}$ to $R_{16}$, $R_{21}$ and $R_{22}$, and Q are as defined in the general formula (1), and X is halogen; when the at least one halophosphite represented by general formula (III) is plural, each of $R_{21}$ and each of $R_{22}$ are identical to or different from each other.

7. The method according to claim 6, wherein a ratio of a mole number of the compound represented by general formula (II), a total mole number of at least one halophosphite represented by general formula (III), and a mole number of triethylamine is 1:(3 to 6):(3 to 6).

8. The method according to claim 1, wherein the first catalyst, the second catalyst, and the third catalyst are identical to each other.

9. The method according to claim 1, wherein a molar ratio of the nickel precursor to the multidentate phosphite ligand is 1:(2 to 20).

10. The method according to claim 1, wherein the nickel precursor is one or a mixture of two or more of elemental nickel, bis (1,5-cyclooctadiene) nickel, nickelocene, carbonyl nickel, allyl (cyclopentadienyl) nickel, tetrakis (triphenylphosphine) nickel, bis-triphenylphosphine dicarbonyl nickel, bis (ethylcyclopentadienyl) nickel, di (methylcyclopentadienyl) nickel, bis (tetramethylcyclopentadienyl) nickel, Ni (acac)$_2$, Ni[P (O-o-C$_6$H$_4$CH$_3$)$_3$]$_3$, and Ni[P (O-o-C$_6$H$_4$CH$_3$)$_3$]$_2$ (C$_2$H$_4$), wherein acac is acetylacetone, P (O-o-C$_6$H$_4$CH$_3$)$_3$ is tri (o-tolyl) phosphite; or the nickel precursor is a combination of a divalent nickel compound and a reducing agent, wherein the divalent nickel compound is a halide, a carboxylate, or an acetylacetonate of divalent nickel, and the reducing agent includes a metal borohydride, a metal alanate, a metal alkyl, Li, Na, K, Zn, or H$_2$.

11. The method according to claim 1, wherein, in the primary hydrocyanation reaction, a molar ratio of butadiene to hydrocyanic acid is 1.0 to 1.5, a ratio of a mole number of hydrocyanic acid to the mole number of the catalyst in terms of zero-valent nickel is (1 to 1000):1, and a reaction temperature is 60 to 140° C., and a reaction pressure is 0.1 to 5.0 MPa;

in the isomerization reaction of branched mononitriles, the ratio of the mole number of the branched mononitrile mixture to the mole number of the catalyst in terms of zero-valent nickel is (1 to 500):1, and the reaction temperature is 80 to 170° C., and the reaction pressure is 0.1 to 5.0 MPa;

in the secondary hydrocyanation reaction, the molar ratio of the linear mononitrile mixture to the hydrocyanic acid is 1.0 to 1.5, the ratio of the mole number of the hydrocyanic acid to the mole number of the catalyst in terms of zero-valent nickel is (20 to 3000):1, and the reaction temperature is 30 to 120° C., and the reaction pressure is 0.1 to 5.0 MPa.

12. The method according to claim 1, wherein a ratio of the mole number of the promoter to the mole number of the catalyst in terms of zero-valent nickel is (0.05 to 2.5):1, and the promoter is a Lewis acid.

* * * * *